United States Patent [19]

Chauvette

[11] 3,962,227
[45] June 8, 1976

[54] 3-HALO CEPHALOSPORINS
[75] Inventor: Robert R. Chauvette, Indianapolis, Ind.
[73] Assignee: Eli Lilly and Company, Indianapolis, Ind.
[22] Filed: Apr. 1, 1974
[21] Appl. No.: 457,150

Related U.S. Application Data
[63] Continuation-in-part of Ser. No. 335,414, Feb. 23, 1973, abandoned.

[52] U.S. Cl.............................. 260/243 C; 424/246
[51] Int. Cl.²....................................... C07D 501/60
[58] Field of Search ............................... 260/243 C

[56] References Cited
UNITED STATES PATENTS
3,705,897  12/1972  Murphy........................... 260/243 C Primary Examiner—Alton D. Rollins
Assistant Examiner—Jose Tovar
Attorney, Agent, or Firm—William B. Scanlon; Everet F. Smith

[57] ABSTRACT

7-Acylamido- and 7-amino-3-halo-3-cephem-4-carboxylic acids, esters and pharmaceutically-acceptable salts and esters thereof are new cephalosporin compounds provided by the reaction of a 7-acylamido-3-hydroxy-3-cephem-4-carboxylic acid ester or a 7-amino-3-hydroxy-3-cephem-4-carboxylic acid ester with an iodinating, fluorinating, chlorinating, or brominating reagent. For example, 7-amino-3-chloro-3-cephem-4-carboxylic acid and 7-phenoxyacetamido-3-chloro-3-cephem-4-carboxylic acid are provided. The 7-acylamido-3-halo cephalosporin acids and pharmaceutically acceptable salts and esters provided are valuable antibiotic compounds having desirable therapeutic properties.

5 Claims, No Drawings

3-HALO CEPHALOSPORINS

CROSS-REFERENCE TO RELATED APPLICATIONS

This application is a continuation-in-part application of co-pending application Ser. No. 335,414 filed Feb. 23, 1973 now abandoned.

BACKGROUND OF THE INVENTION

This invention relates to a novel class of cephalosporin antibiotics. In particular it relates to 3-halo cephalosporins represented by the following generalized formula

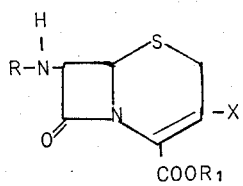

wherein R is hydrogen or an acyl group derived from a carboxylic acid, $R_1$ is hydrogen, a carboxylic acid protecting ester group or a pharmaceutically acceptable ester or salt, and X represents fluoro, chloro, bromo, or iodo.

The compounds of the invention possess the unique structural characteric of a halogen atom directly bonded to the carbon atom in the 3-position of the dihydrothiazine ring. According to the cepham nomenclature system the above depicted compounds are named as 7-amino- or 7-acylamido-3-halo-3-cephem-4-carboxylic acid, salts and esters.

Prior to this invention 3-bromomethyl-3-cephem-4-carboxylic acid esters, U.S. Pat. Nos. 3,647,788 and 3,688,203, and 3-bromomethyl-2-cephem-4-carboxylic acid esters, U.S. Pat. No. 3,637,678 were described. These known 3-bromomethyl compounds are described as useful intermediates for preparing cephalosporin antibiotics. In contrast with these intermediates, the 3-halo-3-cephem-4-carboxylic acids described herein are especially valuable antibiotics.

SUMMARY OF THE INVENTION

U.S. Pat. No. 3,275,626 discloses certain 7-acylamido-3-exomethylenecepham-4-carboxylic acids and esters. In application Ser. No. 278,668 an electrolytic reduction process for the preparation of 3-exomethylene cepham compounds is provided. In my co-pending application Ser. No. 118,941, filed Feb. 25, 1971, another process for preparing 3-exomethylenecepham-4-carboxylic acids and esters is described. According to the described process a 3-thio-substituted-methyl-3-cephem-4-carboxylic acid or ester is reduced to effect the reductive displacement of the 3-thio-substituent and form a 3-exomethylenecepham-4-carboxylic acid or ester. The 7-amino- and 7-acylamido-3-exomethylenecepham-4-carboxylic acid esters are converted to the corresponding 3-hydroxy-3-cephem-4-carboxylic acid esters as described in my copending application Ser. No. 310,191, filed Nov. 28, 1972 now U.S. Pat. No. 3,917,587.

According to the present invention, the 7-amino-, and 7-acylamido-3-hydroxy-3-cephem-4-carboxylic acid esters are halogenated under moderate conditions to provide a 7-amino-, or 7-acylamido-3-halo-3-cephem-4-carboxylic acid ester. By employing readily removable ester groups well known in the cephalosporin art, the 3-halo esters provided are then converted to the free acids by known procedures for removing such ester groups. The 7-amino-3-halo-3-cephem-4-carboxylic acids provided herein can be acylated to provide the 7-acylamido-3-halo-3-cephem-4-carboxylic acid antibiotics. The 7-acylamido-3-halo-3-cephem-4-carboxylic acids provided either by the direct halogenation of a 7-acylamido-3-hydroxy-3-cephem-4-carboxylic acid ester followed by ester removal or by the acylation of a 7-amino-3-halo-3-cephem-4-carboxylic acid or ester are valuable antibiotic compounds which can be used to inhibit the growth of microorganisms pathogenic to animal and plant life.

It is an object of this invention to provide a novel class of cephalosporin antibiotics. In particular it is an object of this invention to provide 7-acylamido-3-halo-3-cephem-4-carboxylic acid antibiotic compounds. It is a further object of this invention to provide the 3-halo substituted cephalosporin nucleus, the 7-amino-3-halo-3-cephem-4-carboxylic acids as well as the esters and salts thereof. A still further object of the present invention is to provide a process for the preparation of the 7-amino- and 7-acylamido-3-halo-3-cephem-4-carboxylic acids described herein.

DETAILED DESCRIPTION

The 3-halo cephalosporin compounds provided by this invention are represented by the following general formula

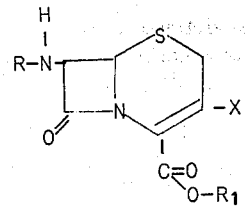

wherein R is hydrogen or an acyl group derived from a carboxylic acid and represented by the formula

wherein
R' is $C_1$-$C_6$ alkyl, $C_1$-$C_3$ haloalkyl, $C_1$-$C_3$ cyanoalkyl, phenyl, methylphenyl, hydroxyphenyl, halophenyl, nitrophenyl, aminophenyl, methoxyphenyl, 5-amino-5-carboxybutyl, or a 5-substituted-amino-5-carboxybutyl ester group of the formula

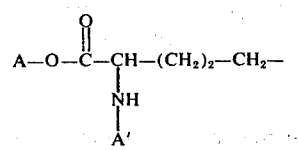

wherein
A is diphenylmethyl, p-nitrobenzyl, benzyl, 2,2,2-trichloroethyl, t-butyl, or p-methoxybenzyl and A' is $C_2$-$C_4$ alkanoyl, $C_2$-$C_4$ haloalkanoyl, benzoyl, halobenzoyl, 2,4-dinitrophenyl, or phthaloyl;
or
R′ is a group of the formula

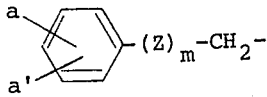

wherein
a and a′ independently are hydrogen, $C_1$-$C_4$ lower alkyl, $C_1$-$C_4$ lower alkoxy, halogen, hydroxy, nitro, amino, or carboxy;
Z is O or S; and
m is 0 or 1; or
R′ is a group of the formula

wherein
P is 2-thienyl, 3-thienyl, phenyl or a substituted phenyl group of the formula

wherein
a and a′ are as defined above, Q is hydroxyl, formyloxy, acetoxy, carboxy, or sulfo; or
R′ is a group of the formula

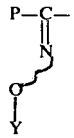

wherein
P has the same meanings as defined above and Y is hydrogen, methyl or acetyl; or
R′ is a group of the formula R″—CH₂—
wherein
R″ is 2-thienyl, 3-thienyl, 2-furyl, 2-oxazolyl, 2-thiazolyl, or 1-tetrazolyl, or
R′ is a group of the formula

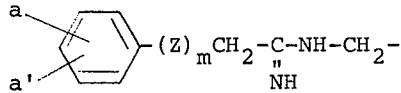

wherein
a, a′, Z and m have the same meanings as defined above;
$R_1$ is hydrogen, benzyl, 4-methoxybenzyl, 4-nitrobenzyl, diphenylmethyl, 2,2,2-trichloroethyl, t-butyl or a pharmaceutically acceptable ester of the formula

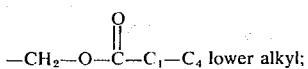

and
X is fluoro, chloro, bromo, or iodo, and when $R_1$ is hydrogen the pharmaceutically acceptable salts thereof.

In the foregoing definition of the compounds provided by this invention the term $C_1$-$C_6$ alkyl refers to the straight and branched chain alkyl hydrocarbon groups such as methyl, ethyl, n-propyl, isopropyl, n-butyl, sec-butyl, n-amyl, isoamyl, n-hexyl, and the like; $C_1$-$C_3$ cyanoalkyl refers to such groups as cyanomethyl, 2-cyanoethyl, 3-cyanoethyl, and 2-cyanopropyl; $C_2$-$C_4$ alkanoyl refers to acetyl, propionyl, butyryl, and the like; $C_2$-$C_4$ haloalkanoyl refers to chloroacetyl, bromoacetyl, 2-chloropropionyl, 3-bromobutyryl, and the like; $C_1$-$C_4$ lower alkyl refers to the straight and branched chain lower alkyl hydrocarbon groups such as methyl, ethyl, n-propyl, iso-propyl, n-butyl, t-butyl, and the like; $C_1$-$C_4$ lower alkoxy refers to methoxy, ethoxy, isopropoxy, n-butoxy, and the like. As used herein the term halogen refers to fluoro, chloro, bromo, and iodo. The term halobenzoyl refers to the chloro and bromo substituted benzoyl groups such as 4-chlorobenzoyl, 4-bromobenzoyl, 2,4-dichlorobenzoyl, and the like.

Illustrative of the groups in the above definition represented by the following formula where m is 0 are

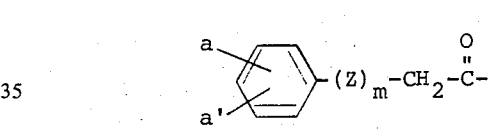

phenylacetyl, 4-methylphenylacetyl, 3-ethylphenylacetyl, 4-isopropylphenylacetyl, 2-methylphenylacetyl, 4-chlorophenylacetyl, 4-nitrophenylacetyl, 4-bromophenylacetyl, 2,4-dichlorophenylacetyl, 3-bromophenylacetyl, 4-iodophenylacetyl, 2-fluorophenylacetyl, 3,4-dihydroxyphenylacetyl, 4-hydroxyphenylacetyl, 3-hydroxyphenylacetyl, 2,6-dimethoxyphenylacetyl, 3-carboxyphenylacetyl, 4-aminophenylacetyl, 3-ethoxyphenylacetyl, 4-methoxyphenylacetyl, 3,4-dimethoxyphenylacetyl, 4-t-butoxyphenylacetyl, 2-carboxyphenylacetyl, 3-chloro-4-methylphenylacetyl, 3-nitrophenylacetyl, and the like. When in the above formula m = 1 and Z represents —O—, illustrative groups are the following. Phenoxyacetyl, 4-hydroxyphenoxyacetyl, 3-hydroxyphenoxyacetyl, 4-chlorophenoxyacetyl, 3-bromophenoxyacetyl, 3-ethylphenoxyacetyl, 4-methylphenoxyacetyl, 3-hydroxy-3-methylphenoxyacetyl, 4-aminophenoxyacetyl, 3-nitrophenoxyacetyl, 2-carboxyphenoxyacetyl, 2-chlorophenoxyacetyl, 4-t-butylphenoxyacetyl, 4-methoxyphenoxyacetyl, 3,4-dimethoxyphenoxyacetyl, 2-aminophenoxyacetyl, 4-isopropoxyphenoxyacetyl, 4-nitrophenoxyacetyl, and like acyl groups. When in the foregoing formula m = 1 and Z represents —S—, illustrative groups are the following. Phenylmercaptoacetyl, 4-chlorophenylmercaptoacetyl, 3-hydroxyphenylmercaptoacetyl, 3,4-dimethylphenylmercaptoacetyl, 4-aminophenylmercaptoacetyl, 3,4-dichlorophenylmercaptoacetyl, 3-bromophenylmercaptoacetyl, 4-fluorophenylmercaptoacetyl, 2,6-difluorophenylmercaptoacetyl, 4-nitrophenylmercaptoacetyl, 3-fluorophenylmercaptoacetyl, and like groups.

When in the formula I R' is a 5-substituted-amino-5-carboxybutyl group,

is representative of esterified amino-protected adipoyl groups wherein the ester group is diphenylmethyl, p-nitrobenzyl, benzyl, p-methoxybenzyl, 2,2,2-trichloroethyl, or t-butyl, and the substituted amino groups can be acetamido, propionamido, chloroacetamido, benzamido, 2,4-dichlorobenzamido, 4-bromobenzamido, phthalimido, 2,4-dimitroanilino and the like.

When in formula I R' represents a group of the formula

illustrative acyl groups,

are the mandeloyl group of the formula

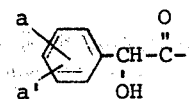

the O-formyl derivative thereof represented by the following formula

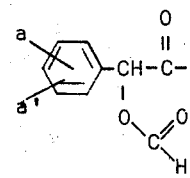

the α-carboxyphenylacetyl group represented by the following formula

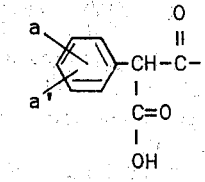

the α-sulfophenylacetyl group represented by the formula

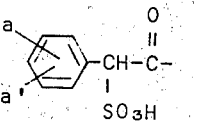

as well as those 2-thienyl and 3-thienyl acyl groups wherein the above formula the phenyl group is replaced with a 2-thienyl or 3-thienyl ring.

When R' is a group of the formula in the syn or anti form

illustrative acyl groups include

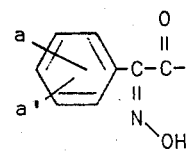

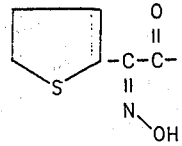

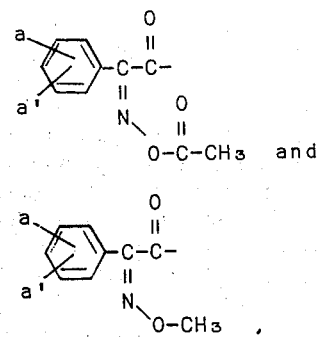

and

Illustrative of the foregoing acyl groups are 4-methylmandeloyl, 4-hydroxymandeloyl, 3-hydroxymandeloyl, 4-aminomandeloyl, 3-bromomandeloyl, 4-chloromandeloyl, 3-methyl-4-fluoromandeloyl, 2-fluoromandeloyl, 4-fluoromandeloyl, 4-methoxymandeloyl, 3,4-dimethyl-O-formylmandeloyl, 4-chloro-O-formylmandeloyl, 3-amino-O-formylmandeloyl, 3-bromo-O-formylmandeloyl, 3,4-dimethoxy-O-formylmandeloyl, O-acetyl mandeloyl, O-acetyl 4-hydroxymandeloyl, α-carboxyl-4-methylphenylacetyl, α-carboxy-3,4-dichlorophenylacetyl, α-carboxy-4-hydroxyphenylacetyl, α-carboxy-2-methoxyphenylacetyl, α-carboxy-4-isopropoxyphenylacetyl, α-carboxy-3-hydroxyphenylacetyl, α-carboxy-4-aminophenylacetyl, α-sulfo-4-methylphenylacetyl, α-sulfo-3,4-dichlorophenylacetyl, α-sulfo-4-chlorophenylacetyl, α-sulfo-4-hydroxyphenylacetyl, α-sulfo-3-methoxyphenylacetyl, α-oximino-4-hydroxyphenylacetyl, α-oximino-3-chlorophenylacetyl, α-oximino-4-carboxyphenylacetyl, α-methoximino-4-methylphenylacetyl, α-methoximino-3,5-dichlorophenylacetyl, α-methoximino-4-hydroxyphenylacetyl, α-methoximino-2-aminophenylacetyl, α-acetyloximinophenylacetyl, α-acetyloximino-2-thienylacetyl, α-acetyloximino-4-hydroxyphenylacetyl, α-oximino-2-thienylacetyl, α-carboxy-2-thienylacetyl, α-carboxy-3- thienylacetyl, α-methoximino-2-thienylacetyl, α-hydroxy-2-thienylacetyl, α-hydroxy-3-thienylacetyl, α-sulfo-2-thienylacetyl, α-formyloxy-2-thienylacetyl, α-acetoxy-2-thienylacetyl and α-methoximino-2-thienylacetyl.

When in the foregoing formula R' represents a group of the formula R''—CH$_2$—, illustrative of the acyl groups of the formula I are the following: 2-thienylacetyl, 3-thienylacetyl, 2-furylacetyl, oxazolyl-2-acetyl, thiazolyl-2-acetyl, and the tetrazolyl-1-acetyl group represented by the following formula

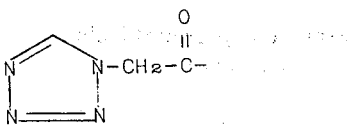

When in Formula I, R' represents the group

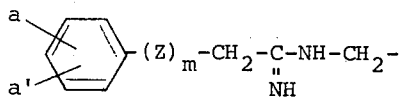

illustrative of the acyl groups,

represented thereby are N-(phenylacetimidoyl)aminoacetyl, N-(phenoxyacetimidoyl)aminoacetyl, N-(phenylmercaptoacetimidoyl)aminoacetyl, N-(4-chlorophenylmercaptoacetimidoyl)aminoacetyl, N-(4-methoxyphenylacetimidoyl)aminoacetyl, N-(2,6-dimethoxyphenylacetimidoyl)aminoacetyl, N-(4-hydroxyphenoxyacetimidoyl)aminoacetyl, N-(4-chlorophenoxyacetimidoyl)aminoacetyl, N-(4-nitrophenylacetimidoyl)aminoacetyl, N-(3,4-dimethylphenylacetimidoyl)aminoacetyl, N-(4-fluorophenoxyacetimidoyl)aminoacetyl, and like mono and disubstituted groups.

A preferred group of 3-halo cephalosporin antibiotics of this invention are represented by the following formula II,

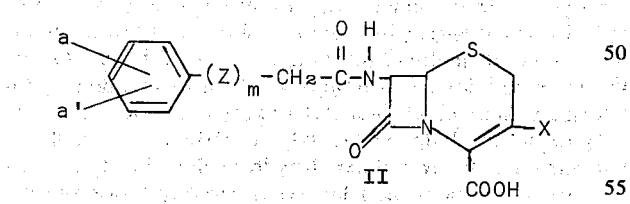

wherein a, a', Z and m have the same meanings as defined above and X is chloro. Illustrative of these preferred compounds are the following.

7-phenylacetamido-3-chloro-3-cephem-4-carboxylic acid,
7-phenoxyacetamido-3-chloro-3-cephem-4-carboxylic acid,
7-(4-hydroxyphenylacetamido)-3-chloro-3-cephem-4-carboxylic acid,
7-(4-chlorophenoxyacetamido)-3-chloro-3-cephem-4-carboxylic acid,
7-(4-methoxyphenoxyacetamido)-3-chloro-3-cephem-4-carboxylic acid, and the pharmaceutically acceptable esters and salts thereof.

Another preferred group of compounds represented by the formula I are those represented by the following formula III.

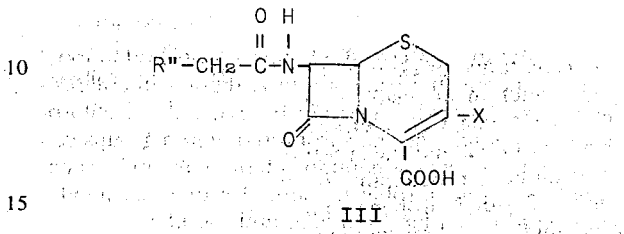

wherein R'' represents 2-thienyl, 3-thienyl, 2-furyl, and 1-tetrazyl and X represents chloro.

Illustrative of the foregoing preferred compounds represented by the formula III are the following.

7-(2-thienylacetamido)-3-chloro-3-cephem-4-carboxylic acid,
7-(2-furylacetamido)-3-chloro-3-cephem-4-carboxylic acid,
7-(3-thienylacetamido)-3-chloro-3-cephem-4-carboxylic acid,
7-(1-tetrazylacetamido)-3-chloro-3-cephem-4-carboxylic acid,
and the pharmaceutically acceptable esters and salts thereof.

A further preferred group of compounds represented by the formula I are those represented by the following formula IV.

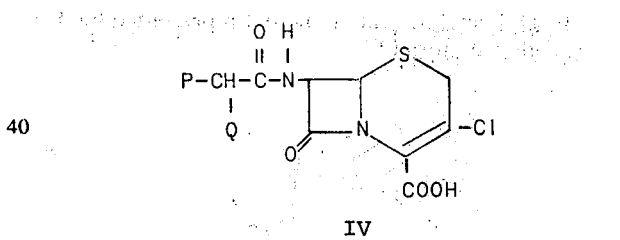

wherein P represents phenyl or a substituted phenyl group as defined in formula I and Q is hydroxy or carboxy. Illustrative of the preferred compounds represented by formula IV are the following.

7-D-mandelamido-3-chloro-3-cephem-4-carboxylic acid,
7-D-(4-chloromandelamido)-3-chloro-3-cephem-4-carboxylic acid,
7-D-(4-hydroxymandelamido)-3-chloro-3-cephem-4-carboxylic acid,
7-D-(4-methoxymandelamido)-3-chloro-3-cephem-4-carboxylic acid,
7-(α-carboxyphenylacetamido)-3-chloro-3-cephem-4-carboxylic acid, and the pharmaceutically acceptable esters and salts thereof.

The 3-halo cephalosporins described herein and represented by the formula I are prepared either by the direct halogenation of a 7-acylamido-3-hydroxy-3-cephem-4-carboxylic acid ester or by the acylation of a 7-amino-3-halo-3-cephem-4-carboxylic acid or ester thereof (formula I, R=H). The 7-amino-3-halo-3-cephem-4-carboxylic acid or ester is prepared either by the direct halogenation of the corresponding 7-amino-3- hydroxy ester or by the cleavage of the 7-acylamido side chain of a 7-acylamido-3-halo cephem ester.

The compounds represented by the formula I wherein X is chloro or bromo are prepared by reacting a 7-acylamido 3-hydroxy-3-cephem ester or a 3-hydroxy-3-cephem nucleus ester in dimethylformamide (DMF) with a reactive chloro or bromo compound which forms with DMF the chloro or bromo dimethyliminium chloride or bromide as represented by the formula

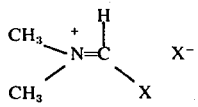

wherein X and X⁻ represent chloro or bromo and chloride or bromide respectively. The reactive halo iminium halide of the above formula is formed in situ and is a highly reactive chlorinating or brominating intermediate. Chloro and bromo compounds which form the above iminium halide include the commonly used chlorinating agents such as phosgene (carbonyl chloride), oxalyl chloride, thionyl chloride, and the phosphorus chlorides, for example, phosphorus trichloride and phosphorus oxychloride (phosphoryl chloride). Brominating reagents which can be employed in the present invention include carbonyl dibromide, oxalyl bromide, thionyl bromide (sulfurous oxybromide), and the phosphorus bromides, phosphorus oxybromide, and phosphorus tribromide. Phosphorus pentachloride can be employed in the preparation of the 3-chloro-3-cephem compounds of the invention, however this reagent concurrently reacts with the 7-acylamido side chain of the starting material to form the imino chloride, the reactive intermediate in the well known cephalosporin side chain cleavage reaction. Accordingly, it is preferable to use one of the other named chlorinating agents.

The chlorination and bormination of a 3-hydroxy cephem ester is conveniently carried out by employing dry DMF as the solvent. The DMF is preferably dried over a molecular sieve before use. A co-solvent can be employed along with excess DMF although such is not required. For example, a co-solvent such as tetrahydrofuran dioxane, methylene chloride, dimethylacetamide or dimethyl sulfoxide can be used along with DMF. The brominating or chlorinating agent such as one of those enumerated above is desirably used in an amount corresponding to two equivalents of the amount of 3-hydroxy cephem ester starting material used. The reaction is carried out by adding the halogenating reagent to a solution of the 3-hydroxycephem ester in dry DMF maintained at a temperature of about 5° to 15°C. and allowing the reaction mixture to stand at room temperature for between 4 and 8 hours or longer. The reaction is initially exothermic and accordingly the reaction vessel is maintained in an ice-water bath to maintain the temperature below about 25°C. during the initial phase of the reaction. Thereafter the reaction mixture is allowed to stand at or about room temperature for the duration of the reaction. The extent to which the reaction has proceeded can be determined by thin layer chromatography.

Alternatively, the chlorination and bromination can be carried out by first preparing a mixture of the halogenating reagent in DMF to preform the haloiminium halide, and then adding the mixture to a solution of the 3-hydroxy-3-cephem ester in DMF, a mixture of DMF and a co-solvent or in a solvent such as dimethylacetamide or tetrahydrofuran.

The 3-chloro- or 3-bromo-3-cephem esters are recovered from the reaction product mixture by pouring the mixture into a water-ethyl acetate mixture and separating the organic phase containing the product. The organic phase is washed, dried and is evaporated to afford the 3-halo-3-cephem ester as an amorphous residue. The product is obtained crystalline in many instances by trituration of the residue with ether or with n-hexane.

The preferred chlorinating and brominating reagents are phosphorus trichloride and phosphorus tribromide.

The 7-amino-3-halo-3-cephem-4-carboxylic acids are preferably obtained by the cleavage of the 7-acyl group of a 7-acylamido-3-halo-3-cephem-4-carboxylic acid ester followed by removal of the carboxylic acid protecting ester group.

The compounds represented by the formula I wherein X is fluoro are prepared by reacting a 7-acylamido-3-hydroxy cephem ester in an inert solvent with the fluorinated tertiary amine, N-(2-chloro-1,1,2-trifluoroethyl)diethylamine. The fluorinated tertiary amine is prepared by reacting diethylamine with chlorotrifluoroethylene as described in *J. Org. Chem.* 29, 2187 (1964); *Tetrahedron Lett.* 23, 1065 (1962) and *Tetrahedron Lett.* 26, 1249 (1962). The fluorination is carried out by reacting the 3-hydroxy cephem ester with an equivalent amount of the fluorinated tertiary amine in an inert solvent, for example, methylene chloride, chloroform, tetrahydrofuran, or any unreactive compound in which the starting material and fluorinating reagent are substantially soluble. The reaction mixture containing the starting 3-hydroxy cephem ester and the fluorinating reagent is heated at a temperature between about 30° and 60°C. for up to about 1 hour.

The 3-fluoro-3-cephem compounds can also be prepared as described in co-pending application Ser. No. 439,206 filed Feb. 6, 1974, now U.S. Pat. No. 3,926,978 by reacting a sulfonate ester of a 7-acylamido-3-hydroxy-3-cephem-4-carboxylic acid ester with an inorganic fluoride such as potassium fluoride in the presence of a crown ether. The starting materials employed in this method, the sulfonate esters of the 3-hydroxy-3-cephem compounds, are prepared as described in co-pending application Ser. No. 439,207 filed Feb. 6, 1974. In this method, a 7-acylamido-3-hydroxy-3-cephem-4-carboxylic acid ester is reacted in an inert solvent with a lower alkylsulfonyl halide or a phenyl or substituted phenylsulfonyl halide in the presence of a hydrogen halide acceptor to form the corresponding 3-lower alkylsulfonyloxy, 3-phenylsulfonyloxy, or substituted 3-phenylsulfonyloxy derivative of the 3-hydroxy substitutent.

The preparation of the alkylsulfonate and arylsulfonate esters of the 3-hydroxy-3-cephem esters is illustrated in the following generalized reaction scheme.

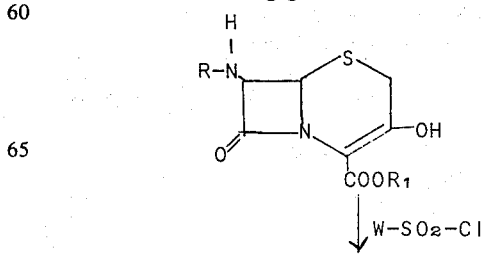

-continued

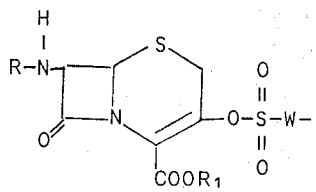

In the above formulae, R represents an acyl group derived from a carboxylic acid, and $R_1$ has the same meanings as previously defined and W is $C_1$-$C_6$ lower alkyl, such as methyl, ethyl, propyl, n-butyl, n-hexyl, and the like, or W is a phenyl group or a substituted phenyl group such as methylphenyl, nitrophenyl, or halophenyl. Representative of the sulfonyl halides which can be employed in the preparation of these sulfonate esters are methanesulfonyl chloride, toluenesulfonyl chloride, p-fluorobenzene sulfonyl chloride, ethanesulfonyl chloride, butanesulfonyl chloride, and the like.

The reaction is carried out in an inert solvent at a temperature between about −5° and 35+C., and preferably between about 15° and 25°C. Inert solvents which can be employed in the sulfonation reaction are solvents which are unreactive with the sulfonyl halide generally aprotic solvents. Solvents which can be employed include amides such as N,N-dimethylformamide and N,N-dimethylacetamide, and ethers such as tetrahydrofuran and dioxane. A preferred solvent for the sulfonation reaction is N,N-dimethylacetamide. The reaction is carried out in the presence of a hydrogen halide acceptor, for example, any of the commonly employed tertiary amines, such as pyridine and triethylamine; alkylene oxides also can be employed, with the most preferred hydrogen halide acceptor being propylene oxide. The tertiary amine hydrogen halide acceptors are less desirable than the alkylene oxides since the double bond in the $\Delta^3$ position of the cephem ring is susceptible to isomerization to the $\Delta^2$ position in the presence of these amines. However, should isomerization to the $\Delta^2$ isomer occur during sulfonate ester formation, the double bond can be isomerized back to the $\Delta^3$ position by oxidizing the $\Delta^2$ isomer of the sulfonate ester to the sulfoxide with a peracid, such as m-chloroperbenzoic acid or peracetic acid. During sulfoxide formation the double bond shifts from the $\Delta^2$ to the $\Delta^3$ position. The sulfoxide then can be reduced in accordance with well known methods, for example, with phosphorus trichloride, to provide the 3-cephem sulfonate ester.

A preferred sulfonate ester for the conversion of the 3-hydroxy-3-cephem-4-carboxylic acid esters to the corresponding 3-fluoro-3-cephem compounds is the methylsulfonate ester (mesylate). Another preferred ester is that formed with p-toluenesulfonyl chloride (tosylate ester). A preferred $C_4$ carboxylic acid protecting ester group in the above described process is the p-nitrobenzyl ester.

The alkyl sulfonate or arylsulfonate esters of a 3-hydroxy-3-cephem ester can be converted to the corresponding 3-fluoro-3-cephem ester by the following general reaction scheme.

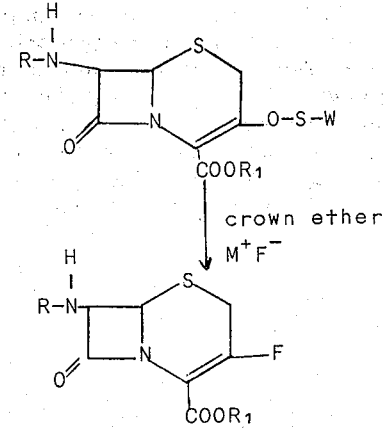

As indicated hereinabove, the sulfonate ester starting materials are defined as having in the 3-position the substituent

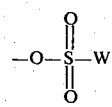

The substituent W, as used herein, defines $C_1$-$C_6$ lower alkyl, phenyl, tolyl, halophenyl, or nitrophenyl. Preferably, W is methyl, phenyl, or p-tolyl. Typical of the sulfonate ester groups thereby defined are methylsulfonyloxy, ethylsulfonyloxy, n-propylsulfonyloxy, isopropylsulfonyloxy, n-butylsulfonyloxy, isobutylsulfonyloxy, t-butylsulfonyloxy, n-amylsulfonyloxy, isoamylsulfonyloxy, t-amylsulfonyloxy, n-hexylsulfonyloxy, isohexylsulfonyloxy, 2,2-dimethylbutylsulfonyloxy, 3,3-dimethylbutylsulfonyloxy, 2,3-dimethylbutylsulfonyloxy, 3-methylpentylsulfonyloxy, phenylsulfonyloxy, p-tolylsulfonyloxy, m-tolylsulfonyloxy, o-tolylsulfonyloxy, o-nitrophenylsulfonyloxy, m-nitrophenylsulfonyloxy, p-nitrophenylsulfonyloxy, p-chlorophenylsulfonyloxy, m-bromophenylsulfonyloxy, p-fluorophenylsulfonyloxy, o-chlorophenylsulfonyloxy, p-bromophenylsulfonyloxy, and the like.

Crown ethers are recognized in the literature, see for example, R. N. Greene, Tetrahedron Letters, No. 18 (1972) pp. 1793–1796. Crown ethers are cyclic structures comprised of a chain of alternating ethylene groups and oxygen atoms. In the process of this invention, an 18-crown-6 ether is employed. The basic unsubstituted 18-crown-6 ether structure is

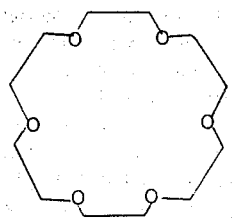

Alternatively, it is named 1, 4, 7, 10, 13, 16-hexaoxacyclooctadecane. The common designation "18-crown-6" defines the total number of atoms in the ring (18) and the total number of oxygens (6) in the ring. Other 18-crown-6 ethers can be employed in the process of this invention. These include, for example dibenzo-18-crown-6 having the formula

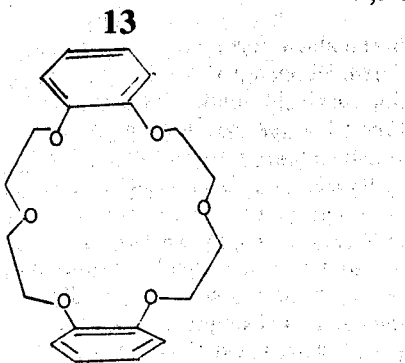

and dicyclohexyl-18-crown-6 having the formula

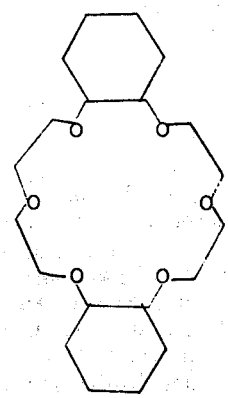

The source of fluorine for use in displacement of the sulfonate ester function is an inorganic fluoride of the formula $M^+F^-$ in which $M^+$ refers to a sodium, potassium or silver ion. Preferably, the fluoride salt which is employed is potassium fluoride.

The conversion of the 3-sulfonyloxy-3-cephem to the 3-fluoro-3-cephem is carried out in an inert solvent, specifically a nitrile or a nitroalkane, preferably acetonitrile, propionitrile, nitromethane, or nitroethane, and, most preferably, acetonitrile, under substantially anhydrous conditions at a temperature of from about −20°C. to about +25°C., and, preferably, from about −15°C., to about +25°C. The 3-sulfonate ester cephalosporin present in the selected solvent is mixed with preferably, a maximum of one equivalent of the inorganic fluoride salt based on the sulfonate ester. Preferably, an equivalent amount of the sulfonate ester and the fluoride salt are employed. The crown ether preferably should be present in the reaction mixture in an amount equivalent on a molar basis to the amount of fluoride salt which is present. An excess of the crown ether can be employed; however, the excess will serve no useful purpose and will constitute simply a waste of valuable reagent. The reaction mixture is maintained at reaction temperature for a period generally of from about 30 minutes to about 3 hours, total time generally being dependent upon the temperature of reaction.

The product which is obtained from the reaction will correspond structurally in every respect to the sulfonate ester starting material with the exception that the group $-O-SO_2-W$ will have been displaced by a fluorine atom.

As mentioned hereinbefore, the initial 3-sulfonate ester cephalosporin reactant can be either a $\Delta^3$-ceph- alosporin, a $\Delta^2$-cephalosporin, or a mixture of the two. The active reactant is the $\Delta^3$-cephalosporin. However, under the conditions of reaction, any $\Delta^2$-cephalosporin which may be present is isomerized to the corresponding $\Delta^3$-cephalosporin, and thus the active reactant is formed in situ from any $\Delta^2$-cephalosporin which may be present initially in the reaction mixture.

The 3-iodo-3-cephem-4-carboxylic acids and esters of the Formula I and prepared by reacting a 7-acylamido-3-hydroxy-3-cephem-4-carboxylic acid ester in DMF with a diiodo triaryl phosphite for example iodotriphenoxyphosphonium iodide or a triaryl phosphate methiodide for example triphenyl phosphate methiodide respectively represented by the formulae

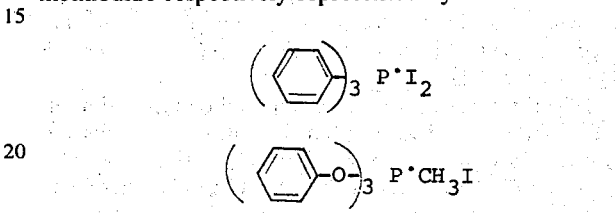

The iodination is carried out in dry DMF at about 20°–35°C. by employing a molar excess of the iodinating reagent. The 3-hydroxy-3-cephem ester and the iodinating agent are allowed to react for about 12 to 15 hours and thereafter the reaction mixture is poured into a mixture of ethyl acetate-water. The organic layer is separated and is washed with a 5% solution of sodium thiosulfate to remove any free iodine present. Following a water wash the organic phase is dried and evaporated. The residue is triturated with ether or n-hexane to obtain the 3-iodo-3-cephem ester.

The iodinating reagents described above are known reagents which have previously been employed for converting hydroxylic compounds to iodo compounds, for example, as described in J. Am. Chem. Soc. 86, 2093 (1964), J. Chem. Soc. (1953) 2224 and J. Chem. Soc. (1954) 2281.

The 3-iodo-7-amino-3-cephem-4-carboxylic acid, the 3-iodo nucleus (formula I, R=H, X=I), is prepared by the cleavage of the 7-acyl group of a 7-acylamido-3-iodo-3-cephem-4-carboxylic acid ester followed by removal of the ester group. The 7-acyl removal is effected by the known phosphorus pentachloride in pyridine method.

As previously mentioned the 3-chloro or 3-bromo cephalosporin compounds of the invention can be prepared either by halogenating a 7-acylamido-3-hydroxy-3-cephem-4-carboxylic acid ester or by acylating a 3-halo-7-amino-3-cephem-4-carboxylic acid or ester. When the former method for preparing the compounds of the invention is chosen, the 7-acylamido group of the starting material is desirably one which does not react with the halogenating agent under the conditions described above. For example, when the acyl moiety in the 7-position of the starting material contains reactive functional groups such as the carboxyl group, the amino group, the sulfonic acid (sulfo) group and the like, such groups are blocked by the formation of an unreactive derivative thereof prior to the halogenation reaction described above. Illustrative of the 7-acylamido-3-hydroxy-3-cephem-4-carboxylic acid esters which can be halogenated without concurrent halogenation in the side chain are the compounds represented by the formula I wherein R is $C_2$-$C_7$ alkanoyl, $C_2$-$C_3$ haloalkanoyl, $C_2$-$C_3$ cyanoalkanoyl, phenoxyacetyl, 2 -thienylacetyl, 3-thienylacetyl, and 2-furylacetyl.

The 7-amino-3-halo-3-cephem compounds of the Formula I, R=H, are best prepared by the cleavage of the 7-acylamido side chain from a 7-acylamido-3-halo-3-cephem-4-carboxylic acid ester by the well known phosphorus pentachloride cleavage reaction. For example, 7-[2-(2-thienyl)acetamido]-3-chloro-3-cephem-4-carboxylic acid p-nitrobenzyl ester is reacted with phosphorus pentachloride in methylene chloride in the presence of pyridine to provide the imino chloride derivative thereof. The imino chloride intermediate is reacted with an alcohol, for example methanol or isobutanol, to provide the corresponding imino ether derivative. Hydrolysis of the imino ether provides the p-nitrobenzyl 7-amino-3-chloro-3-cephem-4-carboxylate hydrochloride.

The starting materials employed in the preparation of the compounds of the present invention are prepared as described in my co-pending application Ser. No. 310,191 filed Nov. 28, 1972. As described therein a 7-acylamido-3-exomethylenecepham-4-carboxylic acid ester or a 7-amino-3-exomethyleneceptham-4-carboxylic acid ester is reacted with ozone in an inert solvent at a temperature between −80 and 0°C. to form the ozonide derivative of the 3-exomethylene double bond. The ozonide intermediate, which is not isolated, is decomposed by reacting the ozonide in situ with a mild reducing agent such as sodium bisulfite, or preferably sulfur dioxide, to provide the corresponding 3-hydroxy-3-cephem-4-carboxylic acid ester.

The ozonolysis of a 7-amino-3-exomethylenecepham-4-carboxylic acid ester or a 7-acylamido-3-exomethylenecepham-4-carboxylic acid ester of the following Formula V is carried out by passing ozone through a solution of the 3-exomethylene-cephem ester in an inert solvent at a temperature between about −80° and 0°C. The exomethylene double bond reacts with ozone to form in situ an intermediate ozonide which is decomposed, as hereinafter described, to form the 3-hydroxy-3-cephem ester of the Formula VI.

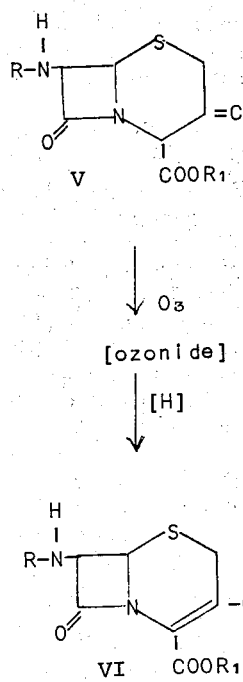

In the above formulae, R is hydrogen or an acyl group derived from a carboxylic acid and which acyl group is non-oxidizable under the described ozonolysis conditions. $R_1$ is an ester forming group and preferably one which is easily removed under hydrogenolysis, or acid or base hydrolysis conditions.

Although the 3-exomethylene cephalosporins can also undergo oxidation with ozone to form the sulfoxide, under the described ozonization conditions the exo double bond reacts preferentially with ozone to form the ozonide. The formation of the sulfoxide occurs as a result of over oxidation. Whereas the exo double bond reacts rapidly with ozone, the reaction at the sulfur atom of the dihydrothiazine ring to form the sulfoxide occurs at a much slower rate. However, the following over oxidation products can be formed in the ozonolysis reaction.

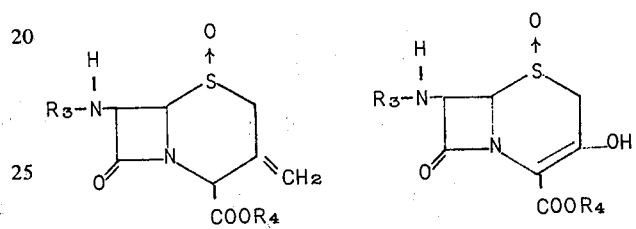

Ozone gas is prepared by means of an ozone generator of the type commonly used in synthetic and analytical chemical work to produce ozone by the action of an electric discharge on oxygen. One such ozone generator is that manufactured by the Welsback Corporation. The ozone is generated in a stream of oxygen which is then passed directly into the reaction vessel. The percentage of ozone contained in the oxygen stream can be varied as desired, for example, by varying the rate of flow of oxygen through the ozonizer as well as by varying the intensity of the electric discharge. The percentage of ozone in the oxygen stream can be determined iodometrically by titrating with sodium thiosulfate the amount of iodine liberated from a standard solution of potassium iodide by ozone from the generator. The percentage of ozone in the oxygen stream is not critical, however for convenience in carrying out the ozonolysis method of this invention an estimate of the amount of ozone flowing into the reaction mixture enables one to determine the time at which the desired reaction should be complete and thus minimizes the formation of over oxidation products.

Alternatively, the ozonolysis reaction can be followed chromatographically. For instance, a small aliquot of the reaction mixture is withdrawn, the ozonide decomposed, and the amount of unreacted starting material and 3-hydroxy-3-cephem product present in the sample is assessed by a comparison of the thin layer chromatogram with that of a known amount of starting material and 3-hydroxy-3-cephem compound.

Inert solvents which can be used in the ozonolysis are those solvents in which the 3-exomethylene cepham esters are at least partially soluble and which are unreactive with ozone under the described conditions. Commonly used organic solvents such as methanol, ethanol, ethyl acetate, methyl acetate, and methylene chloride are satisfactory.

The concentration of the starting material in the inert solvent is not critical and it is preferred to use a solvent volume sufficient to form a complete solution.

The preferred temperature in the ozonolysis reaction is between about −80° and − °C.

When ozonide formation is complete as determined by either method described above, any excess ozone present in the reaction mixture is purged from the mixture by bubbling nitrogen or oxygen through the mixture.

Following the removal of any excess ozone, the ozonide is decomposed by adding to the reaction mixture a mild reducing reagent selected from the group consisting of sodium bisulfite, sulfur dioxide, and trimethyl phosphite to provide the 3-hydroxy-3-cephem-4-carboxylic acid ester. The decomposition is carried out by adding an excess of the reducing reagent and then stirring the reaction mixture at a temperature of about −λ° 80°to 0°C. until the reaction mixture is negative in the potassium iodide-starch test.

A preferred reagent for decomposing the intermediate ozonide is gaseous sulfur dioxide. This reagent is preferred since it is completely volatilized from the reaction mixture during the subsequent work-up and thus does not complicate the recovery of the reaction product.

The 7-acylamido-3-hydroxy-3-cephem-4-carboxylic acid esters are recovered from the reaction mixture by first evaporating the mixture to dryness and thereafter extracting the product from the residue. Alternatively, N-acylated 3-hydroxy-3-cephem esters can be recovered from the organic liquid phase of the decomposition mixture by separating the liquid phase from insolubles, and after washing and drying, the organic layer is evaporated to yield the 3-hydroxy ester.

The 3-hydroxy nucleus ester, a 7-amino-3hydroxy-3-cephem-4-carboxylic acid ester, is best isolated in the form of a salt as for example, the hydrochloride or hydrobromide salt.

When an ester of 7-amino-3-exomethylenecepham-4-carboxylic acid (Formula V, R=H) is ozonized it is preferable to use a salt of this nucleus, for example, the hydrochloride or p-toluenesulfonate salt.

In a specific example of the preparation of a 3-hydroxy-3-cephem ester, p-methoxybenzyl 7-phenoxyacetamido-3-exomethylenecepham-4-carboxylate is dissolved in ethyl acetate and is reacted with ozone at a temperature of about −78°C. The excess ozone is expelled by bubbling oxygen through the cold solution. The ozonide is decomposed by adding excess sodium bisulfite to the reaction mixture at 0°C. with stirring. The organic layer is decanted from the insolubles and is washed, dried and evaporated to yield p-methoxybenzyl 7-phenoxyacetamido-3-hydroxy-3-cephem-4-carboxylate.

In a further example, p-nitrobenzyl 7-amino-3-methylenecepham-4-carboxylate hydrochloride is dissolved in methanol and ozone is bubbled through the solution at a temperature of about −78°C. Excess ozone is purged from the mixture with nitrogen and the ozonide is decomposed by bubbling sulfur dioxide through the mixture. The reaction mixture is evaporated to dryness and the residue, p-nitrobenzyl 7-amino-3-hydroxy-3-cephem-4-carboxylate is obtained as the hydrochloride salt.

The starting materials for the preparation of the 3-exomethylenecepham esters are prepared as described in my co-pending application Ser. No. 118,941, filed Feb. 25, 1971. As described therein, a 7-acylamido cephalosporanic acid is reacted with a sulfur containing nucleophile according to known procedures to effect the nucleophilic displacement of the acetoxy group of the cephalosporanic acid and provide a 7-acylamido-3-thiosubstituted-methyl-3-cephem-4-carboxylic acid. The 3-thiosubstituted cephem product is then reduced with hydrogen in the presence of Raney nickel or with zinc/formic acid in the presence of dimethylformamide to produce the 3-exomethylenecepham acid. For example, 7-phenylacetamidocephalosporanic acid is reacted with potassium ethyl xanthate to yield 7-phenylacetamido-3-ethoxythionocarbonylthiomethyl-3-cephem-4-carboxylic acid which on reduction with zinc/formic acid in the presence of DMF yields 7-phenylacetamido-3-exomethylenecepham-4-carboxylic acid of the formula

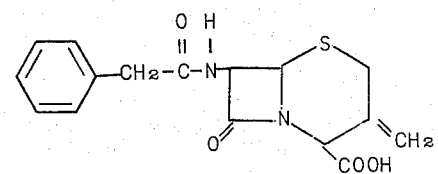

Likewise, there is described the 3-exomethylenecepham nucleus of the formula

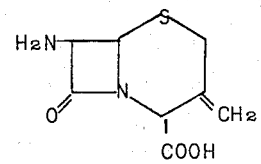

which can be prepared by reacting a 7-acylamido-3-exomethylenecepham-4-carboxylic acid ester with phosphorus pentachloride ($PCl_5$) in methylene chloride in the presence of pyridine to obtain the intermediate imino chloride. The imino chloride is reacted with methanol in the cold to afford the imino ether. The imino ether readily undergoes hydrolysis to provide the 7-amino-3-exomethylenecepham-4-carboxylic acid ester hydrochloride. The ester group is then removed to yield the 3-exomethylenecepham nucleus.

As described above the compounds of the invention as represented by the formula I can be prepared by the acylation of a 7-amino-3-halo-3-cephem-4-carboxylic acid or an ester thereof.

The acylation of these nuclei can be carried out by the known methods used for the acylation of 7-aminocephalosporanic acid or 7-aminodeacetoxycephalosporanic acid. The cephalosporin 3-halo nucleus acids or esters (Formula I, R=H) can be acylated under anhydrous acylation methods as well as in the presence of water. Accordingly, the cephalosporin 3-halo nucleus free acid or an ester thereof can be acylated with a carboxylic acid halide in an aqueous solvent system, for example aqueous acetone, in the presence of a hydrogen halide acceptor such as propylene oxide, pyridine or sodium bicarbonate. The acylation can also be effected by reacting an ester of the halo nucleus with a carboxylic acid in the presence of a condensing agent such as N-ethoxycarbonyl-2-ethoxy-1,2-dihydroquinoline (EEDQ) or dicyclohexylcarbodiimide. Also the 3-halo nucleus ester can be acylated in a mixed anhydride reaction. By yet another known acylation method, the halo nucleus can be acylated with an active ester of a carboxylic acid, for example the pentachlorophenyl ester of a carboxylic acid.

For example, p-nitrobenzyl 7-amino-3-chloro-3-cephem-4-carboxylate is reacted with phenylacetyl chloride in cold aqueous acetone containing sodium bicarbonate to provide p-nitrobenzyl 7-phenylacetamido-3-chloro-3-cephem-4-carboxylate.

Diphenylmethyl 7-amino-3-bromo-3-cephem-4-carboxylate is reacted with phenoxyacetyl chloride in the presence of pyridine to provide diphenylmethyl 7-phenoxyacetamido-3-bromo-3-cephem-4-carboxylate.

p-Methoxybenzyl 7-amino-3-chloro-3-cephem-4-carboxylate is reacted with mandelic O-carboxy-anhydride in ethyl acetate to provide p-methoxybenzyl 7-(D-α-mandelamido)-3-chloro-3-cephem-4-carboxylate.

Illustrative of these derivatives of the acyl groups R′—C=O which can be employed in the acylation of the halo nucleus esters or free acids provided by this invention or the following: thiophene-2-acetyl chloride, phenoxyacetyl chloride, phenylacetyl chloride, oxazole-2-acetyl bromide, thiazole-2-acetyl chloride, tetrazole-1-acetic acid, mandelic acid O-carboxy anhydride, 4-hydroxymandelic acid O-carboxy anhydride, 4-chlorophenoxyacetyl bromide, benzoyl chloride, 2,6-dimethoxybenzoyl chloride, thiophene-3-acetyl chloride, furyl-2-acetyl chloride, the pentachlorophenyl ester of phenylmercapto acetic acid, 4-chlorophenylmercaptoacetyl chloride, and like acylating reagents.

Illustrative of the antibiotic cephalosporins of the Formula I wherein R′ is represented by R″CH$_2$— are the following:

7-[2-(2-thienyl)acetamido]-3-chloro-3-cephem-4-carboxylic acid,
7-[2-(2-thienyl)acetamido]-3-fluoro-3-cephem-4-carboxylic acid,
7-[2-(3-thienyl)acetamido]-3-chloro-3-cephem-4-carboxylic acid,
7-[2-(2-furyl)acetamido]-3-chloro-3-cephem-4-carboxylic acid,
7-[2-(2-furyl)acetamido]-3-bromo-3-cephem-4-carboxylic acid,
7-[2-(2-oxazyl)acetamido]-3-chloro-3-cephem-4-carboxylic acid,
7-[2-(2-thiazyl)acetamido]-3-chloro-3-cephem-4-carboxylic acid,
7-[2-(2-thiazyl)acetamido]-3-bromo-3-cephem-4-carboxylic acid,
7-[2-(1-tetrazyl)acetamido]-3-chloro-3-cephem-4-carboxylic acid,
7-[2-(1-tetrazyl)acetamido]-3-fluoro-3-cephem-4-carboxylic acid, and the benzyl, diphenylmethyl, m-methoxybenzyl, p-nitrobenzyl, 2,2,2-trichloroethyl and tert-butyl esters and the pharmaceutically acceptable esters and non-toxic base addition salts thereof.

The compounds of the Formula I wherein Q is a carboxylic acid group can be prepared for example, by the acylation of a 3-halo-3-cephem nucleus ester with tert-butyl phenylmalonic acid chloride, or with tert-butyl 2-thienylmalonic acid chloride in the presence of a hydrogen halide acceptor such as sodium bicarbonate. For example, tert-butyl 7-amino-3-chloro-3-cephem-4-carboxylate is reacted with 2 equivalents of tert-butyl phenylmalonyl chloride in acetone at a temperature of about 5°C. and in the presence of excess sodium bicarbonate to provide, tert-butyl 7-(α-tert-butyloxycarboxylphenylacetamido)-3-chloro-3-cephem-4-carboxylate. Removal of both tert-butyl ester groups with 90% formic acid provides the diacid, 7-(α-carboxyphenylacetamido)-3-chloro-3-cephem-4-carboxylic acid.

Illustrative compounds represented by the Formula I wherein Q is a carboxy group are 7-(α-carboxyphenylacetamido)-3-chloro-3-cephem-4-carboxylic acid, 7-[2-carboxy-2-(2-thienyl)-acetamido]-3-chloro-3-cephem-4-carboxylic acid, 7-(α-carboxy-4-hydroxyphenylacetamido)-3-chloro-3-cephem-4-carboxylic acid, 7-(α-carboxyphenylacetamido)-3-fluoro-3-cephem-4-carboxylic acid, 7-[2-carboxy-2-(2-thienyl)acetamido]-3-fluoro-3-cephem-4-carboxylic acid, 7-(α-carboxyphenylacetamido)-3-bromo-3-cephem-4-carboxylic acid, 7-(α-carboxy-4-chlorophenylacetamido)-3-chloro-3-cephem-4-carboxylic acid, 7-(α-carboxy-3,4-dimethoxyphenylacetamido)-3-chloro-3-cephem-4-carboxylic acid, 7-[2-carboxy-2-(3-thienyl)acetamido]-3-chloro-3-cephem-4-carboxylic acid, 7-(α-carboxy-3-hydroxyphenylacetamido)-3-chloro-3-cephem-4-carboxylic acid and the benzyl, diphenylmethyl, p-methoxybenzyl, p-nitrobenzyl, 2,2,2-trichloroethyl and tert-butyl esters and the pharmaceutically acceptable non-toxic base addition salts thereof.

The α-sulfo-acylamido-3-halo-cephem compounds of the Formula I wherein Q is a sulfo group (—SO$_3$H) are prepared by following the acylation procedures employed for the preparation of α-sulfobenzylpenicillins described by U.S. Patent No. 3,660,379 and in the *J. Med. Chem.*, 15 (11), 11–5 (1972); ibid, p. 1108. For example, 7-amino-3-chloro-3-cephem-4-carboxylic acid is reacted with α-sulfophenylacetyl chloride in a mixture acetone and water containing an excess of sodium bicarbonate to yield 7-(α-sulfophenylacetamido)-3-chloro-3-cephem-4-carboxylic acid. Examples of α-sulfoacylamido-3-halo-cephems of the present invention are, 7-(α-sulfo-3-chlorophenylacetamido)-3-chloro-3-cephem-4-carboxylic acid,
7-(α-sulfo-4-hydroxyphenylacetamido)-3-chloro-3-cephem-4-carboxylic acid,
7-(α-sulfo-4-methoxyphenylacetamido)-3-bromo-3-cephem-4-carboxylic acid,
7-[2-sulfo-2-(2-thienyl)acetamido]-3-chloro-3-cephem-4-carboxylic acid,
7-[2-sulfo-2-(3-thienyl)acetamido]-3-chloro-3-cephem-4-carboxylic acid,
7-[2-sulfo-2-(2-thienyl)acetamido]-3-fluoro-3-cephem-4-carboxylic acid,
7-(α-sulfo-3,4-dimethylphenylacetamido)-3-chloro-3-cephem-4-carboxylic acid and the benzyl, diphenylmethyl, p-methoxybenzyl, p-nitrobenzyl, 2,2,2-trichloroethyl and tert-butyl esters and the pharmaceutically acceptable non-toxic base addition salts thereof.

The compounds of the Formula I wherein R is an acyl group of the formula

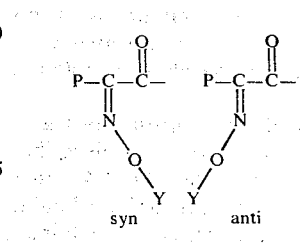

are prepared by the acylation of a 3-halo-3-cephem-nucleus ester with an α-methoximino or α-acetyloximino glyoxamoyl chloride wherein Y is methyl or acetyl. The α-oximino compounds, Y=H, are prepared by the base hydrolysis of the α-acetyloximino compounds. For example, p-nitrobenzyl 7-(α-methoximinophenylglyoxamido)-3-chloro-3-cephem-4-carboxylate is prepared by the acylation of p-nitrobenzyl 7-amino-3-chloro-3-cephem-4-carboxylate with α-methoximinophenylglyoxamoyl chloride in an acetone-water mixture containing an excess of sodium bicarbonate.

p-Nitrobenzyl 7-amino-3-chloro-3-cephem-4-carboxylate is acylated with α-acetytoximinophenylglyoxamoyl chloride in acetone in the presence of pyridine to yield p-nitrobenzyl 7-(α-acetyloximinophenylglyoxamido)-3-chloro-3-cephem-4-carboxylate.

The α-oximino compounds, Y=H, are obtained by the mild base hydrolysis of the α-acetyloximino compounds. For example, p-nitrobenzyl 7-(α-acetyloximinophenylglyoxamido)-3-chloro-3-cephem-4-carboxylate is reacted in aqueous acetone for 12 hours at room temperature with one mole of sodium hydroxide to yield p-nitrobenzyl 7-(α-oximinophenylglyoxamido)-3-chloro-3-cephem-4-carboxylate.

The foregoing is illustrated by the following reaction scheme which depicts arbitrarily the syn form.

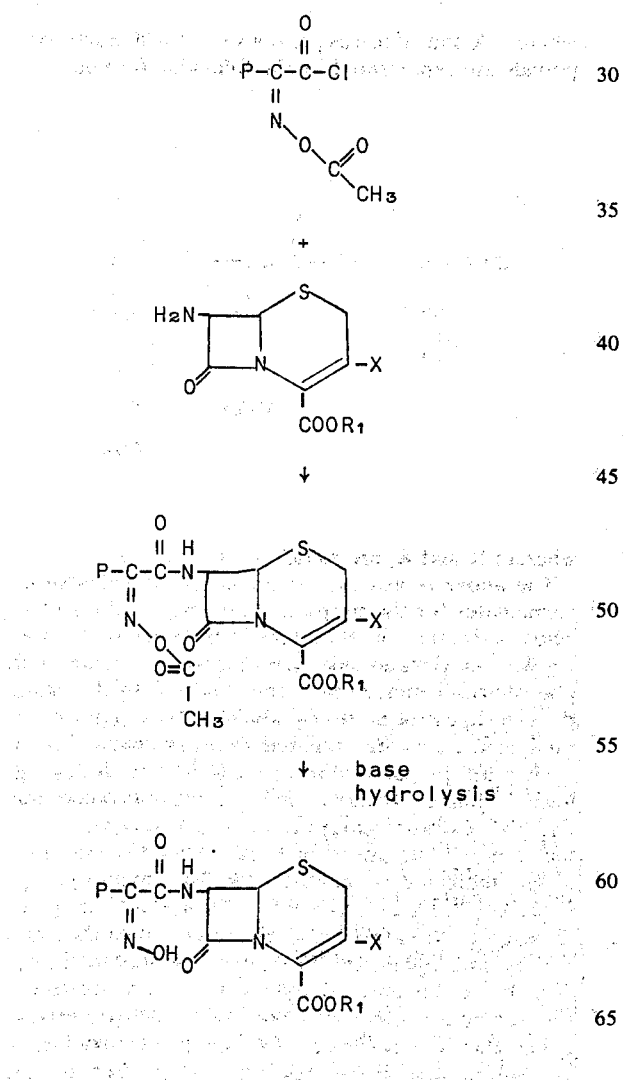

wherein P, $R_1$ and X have the same meanings as previously defined.

Illustrative of the 7-(α-oximino, α-acetyloximino- and α-methoximinoarylglyoxamido-3-halo cephalosporins provided by this invention are 7-(α-oximinophenylglyoxamido)-3-chloro-3-cephem-4-carboxylic acid,
7-(α-methoxyimino-4-chlorophenylglyoxamido)-3-chloro-3-cephem-4-carboxylic acid,
7-(α-oximino-4-hydroxyphenylglyoxamido)-3-chloro-3-cephem-4carboxylic acid,
7-[α-oximino-2-(2-thienyl)glyoxamido]-3-chloro-3-cephem-4-carboxylic acid,
7-(α-oximinophenylglyoxamido)-3-fluoro-3-cephem-4-carboxylic acid,
7-(α-methoximinophenylglyoxamido)-3-bromo-3-cephem-4-carboxylic acid,
7-[α-oximino-2-(3-thienyl)glyoxamido]-3-chloro-3-cephem-4-carboxylic acid,
7-[α-oximino-2-(2-thienyl)glyoxamido]-3-fluoro-3-cephem-4-carboxylic acid
7-(α-acetyloximinophenylglyoxamido)-3-chloro-3-cephem-4-carboxylic acid,
7-(α-acetyloximinophenylglyoxamido)-3-fluoro-3-cephem-4-carboxylic acid,
7-[α-acetyloximino-2-(2-thienyl)glyoxamido]-3-chloro-3-cephem-4-carboxylic acid, and the benzyl, diphenylmethyl, p-methoxybenzyl, p-nitrobenzyl, 2,2,2-trichloroethyl and tertbutyl esters and the pharmaceutically acceptable esters and nontoxic base addition salts thereof.

The antibiotic compounds of the Formula I, wherein R' is a substituted imidoyl aminoacetamido group of the formula

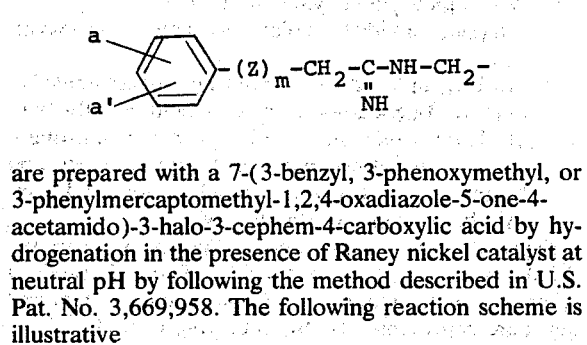

are prepared with a 7-(3-benzyl, 3-phenoxymethyl, or 3-phenylmercaptomethyl-1,2,4-oxadiazole-5-one-4-acetamido)-3-halo-3-cephem-4-carboxylic acid by hydrogenation in the presence of Raney nickel catalyst at neutral pH by following the method described in U.S. Pat. No. 3,669,958. The following reaction scheme is illustrative

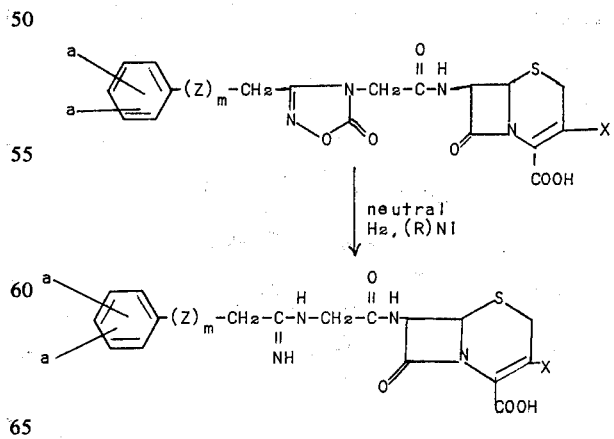

wherein a, a', Z, m and X are as previously defined.

The substituted oxadiazole 3-halocephalosporin is prepared by acylation of a 3-halo nucleus acid or ester, for example 7-amino-3-chloro-3-cephem-4-carboxylic acid, with a 3-substituted 1,2,4-oxadiazole-5-one-4-acetyl chloride under conventional acylation conditions such as those described in U.S. Pat. No. 3,669,958.

Alternatively these intermediates can be prepared by reacting a 7-haloacetamido-3-halo-3-cephem-4-carboxylic acid or ester (Formula I, R=chloro or bromoacetyl) with the 3-substituted 1,2,4-oxadiazole-5-one in the presence of a hydrogen halide acceptor such as pyridine.

Illustrative of the 7-substituted-imidoyl aminoacetamido-3-halo cephalosporin antibiotics represented by the Formula are, 7-[N-(phenoxyacetimidoyl)aminoacetamido]-3-chloro-3-cephem-4-carboxylic acid,
7-[N-(phenylacetimidoyl)aminoacetamido]-3-chloro-3-cephem-4-carboxylic acid,
7-[N-(phenylmercaptoacetimidoyl)aminoacetamido]-3-chloro-3-cephem-4-carboxylic acid,
7-[N-(4-chlorophenylmercaptoacetimidoyl)aminoacetamido]-3-chloro-3-cephem-4-carboxylic acid,
7-[N-(phenylacetimidoyl)aminoacetamido]-3-fluoro-3-cephem-4-carboxylic acid,
7-[N-phenoxyacetimidoyl)aminoacetamido]-3-bromo-3-cephem-4-carboxylic acid,
7-[N-(4-hydroxyphenoxyacetimidoyl)aminoacetamido]-3-chloro-3-cephem-4-carboxylic acid,
7-[N-(4-chlorophenoxyacetimidoyl)aminoacetamido]-3-chloro-3-cehem-4-carboxylic acid,
7-[N-(4-nitrophenylacetimidoyl)aminoacetamido]-3-chloro-3-cephem-4-carboxylic acid, and the benzyl, diphenylmethyl, p-methoxybenzyl, p-nitrobenzyl, 2,2,2-trichloroethyl and tertbutyl esters and the pharmaceutically acceptable esters and non-toxic base addition salts thereof.

Especially useful compounds of this invention are the 3-halo nucleus esters and acids of the Formula I wherein R is hydrogen. The 3-halo nucleus esters and acids are represented by the following formula

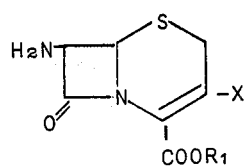

wherein X and $R_1$ are as previously defined. When $R_1$ is hydrogen, the zwitterionic form of the compound can exist as illustrated below.

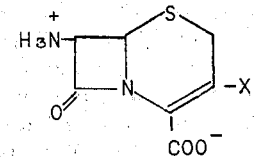

Another especially useful group of compounds provided herein are represented by the Formula I wherein R is 5-amino-5-carboxyvaleryl or an esterified amino-protected 5-amino-carboxyvaleryl group represented by the formula

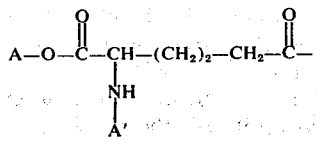

wherein A and A' are as previously defined. Such compounds are represented by the following formula

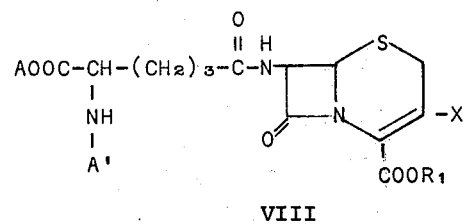

VIII wherein X and $R_1$ are as defined previously.

The above represented compounds are valuable intermediates for the preparation of the 3-halo nucleus acids and esters in that they can undergo the well known 7-acylamido side-chain cleavage reaction with phosphorus pentachloride and pyridine by following the cleavage procedures by which 7-aminocephalosporanic acid esters are prepared with cephalosporin C.

They are prepared with cephalosporin C in the following manner. Initially, the side-chain amino group and both carboxyl groups of cephalosporin C are protected with such groups as A and A' and then the protected molecule is reacted with a sulfur containing nucleophile, for example, potassium ethyl xanthate or thiourea to form the 3-thio-substituted methyl derivative by nucleophilic displacement of the acetoxy function of the 3-acetoxymethyl group. Thereafter the 3-thio-substituted methyl-3-cephem ester is reduced with either Raney nickel in the presence of hydrogen or zinc/formic acid in the presence of DMF to effect the reductive displacement of the 3-thio substituent and provide the 3-exomethylenecepham ester. The above reaction sequence is described in my co-pending application Ser. No. 118,941, filed Feb. 25, 1971.

The 3-exomethylenecepham ester is then reacted with ozone and the ozonide decomposed to form the 3-hydroxy-3-cephem ester according to the method described previously. the 3-hydroxy ester is then halogenated according to the method of this invention to provide a compound of the above formula VIII.

Cleavage of the protected 7-acyl side-chain with $PCl_5$/pyridine/isobutanol or methanol affords the 3-halo nucleus ester of the formula VII. Cleavage of the 7-acyl group can also be carried out with nitrosyl chloride by the method described in U.S. Pat. No. 3,188,311, when the amino adipoyl group is unprotected.

Illustrative of the compounds represented by the above formula VIII are diphenylmethyl 7-[5-diphenylmethyloxycarbonyl-5-(2,4-dichlorobenzamido)valeramido]-3-chloro-3-cephem-4-carboxylate, diphenylmethyl 7-(5-diphenylmethyl-5-chloroacetamidovaleramido)-3-chloro-3-cephem-4-carboxylate, p-nitrobenzyl 7-(5-p-nitrobenzylmethyloxycarbonyl-5-propionamido valeramido)-3-chloro-3-cephem-4-carboxylate, diphenylmethyl 7-[5-diphenylmethyloxycarbonyl-5-(4-chlorobenzamido)valeramido]-3-chloro-3-cephem-4-carboxylate, p-nitrobenzyl 7-(5-p-nitrobenzyloxycarbonyl-5-acetamidovaleramido)-3-chloro-3-cephem-4-carboxylate and diphenylmethyl 7-[5-diphenylmethyloxycarbonyl-5-(2,4-dichlorobenzamido)valeramido]-3-bromo-3-cephem-4-carboxylate.

Examples of the 7-amino-3-halo-3-cephem acids and esters which are provided are the following.

7-amino-3-chloro-3-cephem-4-carboxylic acid,
7-amino-3-bromo-3-cephem-4-carboxylic acid,
7-amino-3-fluoro-3-cephem-4-carboxylic acid,
7-amino-3-iodo-3-cephem-4-carboxylic acid,
diphenylmethyl 7-amino-3-chloro-3-cephem-4-carboxylate,
p-nitrobenzyl 7-amino-3-chloro-3-cephem-4-carboxylate,
p-nitrobenzyl 7-amino-3-bromo-3-cephem-4-carboxylate,
p-methoxybenzyl 7-amino-3-fluoro-3-cephem-4-carboxylate,
2,2,2-trichloroethyl 7-amino-3-chloro-3-cephem-4-carboxylate,
benzyl 7-amino-3-bromo-3-cephem-4-carboxylate
and the like.

The term pharmaceutically acceptable esters as used herein refers to the $C_1$-$C_4$ straight and branched chained alkanoyloxymethyl esters such as acetoxymethyl, propionyloxymethyl and pivaloyloxymethyl esters. These esters of the 7-acylamido-3-halo-3-cephem-4-carboxylic acids possess antibiotic activity at levels akin to those of the free acid form of the cephalosporin compound and can be used in place of the antibiotic in the free acid form. In contrast, the other ester groups within the definition of $R_1$, namely the benzyl, benzhydryl, p-methoxybenzyl, p-nitrobenzyl, 2,2,2-trichloroethyl and t-butyl esters, do not possess any significant antibiotic activity.

The 7-acylamido-3-halo-3-cephem-4-carboxylic acids (Formula I, R=R'—C=O, $R_1$=H)

are useful antibiotic compounds for combating infections attributable to gram-positive and gram-negative organisms. The compounds can be administered by injection (s.c. or i.m.) in the free acid form or in the form of a pharmaceutically accepteable ester or nontoxic acid addition salt. Salts formed with the free acids and inorganic bases such as sodium bicarbonate, potassium carbonate, sodium hydroxide and calcium hydroxide provide the sodium, potassium and calcium salts which can be formulated for administration for example, as isotonic solutions or as liquid suspensions.

The pharmaceutically acceptable esters, for example the acetoxymethyl esters, are prepared by reacting a 7-acylamido-3-halo-3-cephem-4-carboxylic acid alkali metal salt such as the potassium salt with the alkanoyloxymethyl halide such as acetoxymethyl chloride in aqueous acetone.

The in vitro antimicrobial activity of the 3-halo cephalosporins is illustrated by the data in the following tables. Table I contains the antimicrobial activity for 7-[2-(2-thienyl)acetamido]-3-chloro-3-cephem-4-carboxylic acid obtained in the standard Disc-plate method. The numerical values are the diameter in millimeters of the zones of inhibition observed with the named organisms.

TABLE I

ANTIBIOTIC ACTIVITY OF
7-[2-(2-Thienyl)acetamido]-
3-chloro-3-cephem-4-carboxylic acid

| Test Organism | Zone of Inhibition (diameter in mm) Concentration (mg/ml) | | |
|---|---|---|---|
| | 1.0 | 0.1 | 0.01 |
| Staphylococcus aureus | 31 | 29 | 20 |
| Bacillus subtilis | 48 | 40 | 24 |
| Sarcina lutea | 37 | 28 | 21 |
| Mycobacterium avium | 14 | — | — |
| Proteus vulgaris | 17 | 12H[1] | — |
| Salmonella gallinarum | 32 | 22 | — |
| Escherichia coli | 24 | 19 | Tr[2] |
| Klebsiella pneumoniae | 36 | 27 | 13 |
| Pseudomonas solanacearcum | 28 | 21 | — |

[1]H = hazy zone of inhibition
[2]Tr = trace zone of inhibition

The following Table II lists the minimum inhibitory concentration (MIC) for 7-[2-(2-thienyl)acetamido]-3-chloro-3-cephem-4-carboxylic acid against penicillin resistant Staphylococcus both in the presence of and absence of serum. The MIC values were obtained by the Gradient Plate technique carried out essentially as described by Bryson and Szybalski, Science, 116, 45 (1952).

TABLE II

ANTIBIOTIC ACTIVITY vs.
Penicillin Resistant Staphylococcus

| Clinical Isolate | Minimum Inhibitory Concentration (mcg/ml) | |
|---|---|---|
| | No Serum | Serum |
| V 41 | 5.0 | 7.0 |
| V 32 | 8.4 | >20 |
| X 400[1] | >20 | >20 |
| V 84 | 0.8 | 1.0 |
| X 1.1 | 0.2 | <0.1 |

[1]Methicillin resistant Staphylococcus

In Table III, below, the MIC values for the test compound of Tables I and II against representative gram-negative organisms is presented. The data were obtained by the Gradient Plate technique.

Table III

| Test Organism | Antibiotic Activity vs. Gram-Negative Organisms Minimum Inhibitory Conc. (mcg/ml) |
| --- | --- |
| Shigella sp. | 25 |
| Escherichia coli | 18.5 |
| Klebsiella pneumoniae | 0.6 |
| Aerobacter aerogenes | 0.8 |
| Salmonella heidelberg | 0.8 |
| Pseudomonas aeruginosa | >200 |
| Serratia marcescens | >200 |

In Table IV below, the in vitro antimicrobial activity of 7-[2-(2-thienyl)acetamido]-3-bromo-3-cephem-4-carboxylic acid is presented for several illustrative microorganisms. The data presented were obtained in the standard disc-plate method with the numerical values recording the diameter in millimeters of the zones of inhibition observed with the named microorganisms.

TABLE IV

ANTIBIOTIC ACTIVITY OF
7-[2-(2-THIENYL)ACETAMIDO]-
3-BROMO-3-CEPHEM-4-CARBOXYLIC ACID

| Test Organism | Zone of Inhibition[1] (diameter in mm) Concentration (mg./ml.) | | |
| --- | --- | --- | --- |
|  | 1.0 | 0.1 | 0.01 |
| Staphylococcus aureus | 27 | 25 | 22 |
| Bacillus subtilis | 37 | 38 | 23 |
| Sarcina lutea | 32 | 33 | 17 |
| Mycobacterium avium | 23 | h 42 | h 33 |
| Saccharomyces pastorianus | — | — | — |
| Neurospora sp. | — | — | — |
| Candida albicans | — | — | — |
| Bacillus subtilis | 60 | 50 | 43 |
| Trichophyton mentagrophytes | — | — | — |
| Proteus vulgaris | 28 | 20 | h 11 |
| Salmonella gallinarum | 30 | 15 | — |
| Escherichia coli | 23 | 14 | — |
| Pseudomonas aeruginosa | — | — | — |
| Klebsiella pneumoniae | 28 | 19 | 11 |
| Serratia marcescens | — | — | — |
| Pseudomonas solanacearcum | 31 | h 20 | — |
| Escherichia coli | 27 | 18 | h 11 |

*Synthetic medium
[1]An h = hazy zone
A dash indicates no observed zone of inhibition The following Table V lists the minimum inhibitory concentration (MIC) for the antibiotic 7-[2-(2-thienyl)acetamido]-3-bromo-3-cephem-4-carboxylic acid against penicillin resistant strains of Staphylococcus in the absence of serum. The inhibitory concentrations were obtained by the Gradient Plate method.

TABLE V

ANTIBIOTIC ACTIVITY VS.
PENICILLIN RESISTANT STAPHYLOCOCCUS

| Clinical Isolate | Minimum Inhibitory Concentration (mcg./ml.) |
| --- | --- |
| V 41 | 0.5 |
| V 32 | 0.6 |
| X 400[1] | >20 |
| V 84 | 0.4 |
| X 1.1 | 0.3 |

[1]Methicillin resistant Staphylococcus

The minimum inhibitory concentrations for 7-[2-(2-thienyl)acetamido]-3-bromo-3-cephem-4-carboxylic acid against representative gram-negative bacteria is presented in Table VI. The data were obtained by the Gradient Plate Method.

TABLE VI

ANTIBIOTIC ACTIVITY OF
7-[2-(2-THIENYL)ACETAMIDO]-
3-BROMO-3-CEPHEM-4-CARBOXYLIC ACID
VS.
GRAM-NEGATIVE BACTERIA

| Test Organism | Minimum Inhibitory Concentration (mcg./ml.) |
| --- | --- |
| Shigella sp. | 19.8 |
| Escherichia coli | 20.8 |
| Klebsiella pneumoniae | 1.0 |
| Aerobacter aerogenes | 1.0 |
| Salmonella heidelberg | 1.0 |
| Pseudomonas aeruginosa | >200 |
| Serratia marcescens | >200 |

The antibiotic activity of the O-formyl ester of 7-(D-mandelamido)-3-chloro-3-cephem-4-carboxylic acid is demonstrated by the data presented in the following tables. Tables VII and VIII list the minimum inhibitory concentrations of the test compound effective against representative penicillin resistant Staphylococcus strains, while Table VII lists the MIC values obtained against representative gram-negative microorganisms. The data were obtained by the Gradient Plate method.

TABLE VII

ANTIBIOTIC ACTIVITY VS.
PENICILLIN RESISTANT STAPHYLOCOCCUS

| Clinical Isolate | Minimum Inhibitory Concentration (mcg./ml.) | |
| --- | --- | --- |
|  | No Serum | Serum |
| V 41 | 5.8 | >20 |
| V 32 | 8.0 | >20 |
| X 400[1] | >20 | >20 |
| V 84 | 0.4 | 1.0 |
| X 1.1 | <0.1 | <0.1 |

[1]Methicillin resistant Staphylococcus

TABLE VIII

ANTIBIOTIC ACTIVITY VS.
GRAM-NEGATIVE ORGANISMS

| Test Organism | Minimum Inhibitory Concentration (mcg./ml.) |
| --- | --- |
| Shigella sp. | 4.0 |
| Escherichia coli | 6.3 |
| Klebsiella pneumoniae | 1.0 |
| Aerobacter aerogenes | 0.7 |
| Salmonella heidelberg | 0.6 |
| Pseudomonas aeruginosa | >200 |
| Serratia marcescens | 160 |

In Table IX which follows, the MIC values against a spectrum of microorganisms obtained with the test compound are presented. The test method was the standard agar dilution method.

TABLE IX

ANTIBIOTIC SPECTRUM OF 7-[D-(O-FORMYL)MANDELAMIDO]-3-CHLORO-3-CEPHEM-4-CARBOXYLIC ACID

| Test Microorganism | Minimum Inhibitory Concentration (mcg./ml.) |
|---|---|
| Staphylococcus aureus 3055 | >0.25 |
| Staphylococcus aureus 3074 | 1 |
| Streptococcus faecalis X66 | 64 |
| Proteus morganii PR15 | 4 |
| Salmonella typhosa SA12 | 0.5 |
| Klebsiella pneumoniae KL14 | 4 |
| Enterobacter aerogenes EB17 | 128 |
| Serratia marcescens SE3 | >128 |
| Escherichia coli EC14 | 8 |
| Citrobacter freundii | >128 |
| Pseudomonas aeruginosa X239 | 128 |
| Bordetella bronchiseptica 16 | 64 |
| Salmonella typhimurium | 1 |
| Pseudomonas solanacearcum X185 | 128 |
| Erwinia amylovora | >128 |
| Candida tropicalis A17 | >128 |
| Trichophyton mentagrophytes 27 | >128 |
| Aspergillus flavus E | >128 |
| Ceratocystis ulmi | >128 |

The 7-acylamido-3-halo-3-cephem-4-carboxylic acid esters (Formula I, R = R'—C=O, $R_1$ = ester)

are useful as intermediates in the preparation of the free acid antibiotic forms of the compounds. Ester forming groups within the definition of $R_1$ are all known groups commonly employed to protect the $C_4$ carboxylic acid group of the cephalosporin molecule while reactions involving other groups in the molecule are performed. These ester forming groups are readily removed to provide the free acid by known reduction or hydrolysis procedures. For example, the p-nitrobenzyl ester group is removed via catalytic hydrogenolysis over palladium on carbon (U.S. Pat. No. 3,632,850); the diphenylmethyl group (benzhydryl) is removed with trifluoroacetic acid in anisole at about 10°C.; the p-methoxybenzyl group is removed with trifluoroacetic acid at about 10°C. [J. Org. Chem., 36, 1259 (1971)]; the 2,2,2-trichloroethyl group is removed with zinc and acid [J. Am. Chem. Soc. 88, 852 (1966)]; the benzyl ester group is removed via catalytic hydrogenolysis over palladium catalyst [U.S. Pat. No. 3,197,466, J. Org. Chem. 27, 1381 (1962)]; and the tert-butyl group is removed as described in J. Med. Chem., 9, 444 (1966).

The 7-amino-3-halo-3-cephem-4-carboxylic acids and esters (Formula I, R = H) are valuable intermediates useful in preparing the 3-halo antibiotics. As previously described these 3-halo nucleus acids and esters are acylated by following conventional N-acylation procedures to provide the 7-acylamido-3-halo-3-cephem-4-carboxylic acids or esters.

The following Examples are provided to further illustrate the compounds of the invention and the methods and procedures employed in their preparation.

A. PREPARATION OF STARTING MATERIALS

Example 1 p-Nitrobenzyl 7-amino-3-methylenecepham-4-carboxylate hydrochloride

To a solution of 965 mg. (2 mmole) of p-nitrobenzyl 7-phenoxyacetamido-3-methylenecepham-4-carboxylate in 10 ml. of methylene chloride were added 175 mg of dry pyridine and 460 mg. of phosphorus pentachloride and the mixture was stirred at room temperature for 6 hours. One ml. of isobutanol was added to the mixture which was then stored at 0°C. overnight. The reaction product, p-nitrobenzyl 7-amino-3-methylenecepham-4-carboxylate hydrochloride, which formed as a crystalline precipitate was filtered to yield 430 mg. (58% yield).

Elemental Analysis for $C_{15}H_{16}N_3O_5SCl$: Theory: C, 46.69; H, 4.18; N, 10.89. Found: C, 46.40; H, 4.20; N, 10.62

I.R. (Nujol Mull) Carbonyl absorption at 5.65 ($\beta$-lactam) and 5.75 (ester) microns. N.M.R. (DMSO $d_6$) signals at 6.34 (2d, 2H, $C_2$—$H_2$), 4.98 (d, 1H, $C_6$—H); 4.7–4.4 (m, 6H, $C_4$—H, ester $CH_2$, $C_4$—$CH_2$ and $C_7$—H); and 2.4–1.6 (m, 4H, aromatic H) tau.

EXAMPLE 2 p-Nitrobenzyl 7-amino-3-methylenecepham-4-carboxylate p-toluenesulfonate salt

To a solution of 965 mg. of p-nitrobenzyl 7-phenoxyacetamido-3-methylenecepham-4-carboxylate in 10 ml. of methylene chloride were added 175 mg. of dry pyridine and 460 mg. of phosphorus pentachloride and the mixture was stirred for five hours at room temperature. Thereafter the reaction mixture was cooled to 0°C. and 50 ml. of cold methanol were added. Following a stirring period of one-hour at room temperature the reaction mixture was evaporated in vacuo to remove the solvents and the residual reaction product mixture was dissolved in a mixture of ethyl acetate and water. The pH was adjusted to pH 7 and the ethyl acetate layer was separated and was washed with water and dried. One equivalent of p-toluene sulfonic acid was added to the dried solution and on cooling 600 mg. of p-nitrobenzyl 7-amino-3-methylenecepham-4-carboxylate p-toluenesulfonate formed as a crystalline precipitate. The product was purified by recrystallization from a mixture of 12 ml. of methanol 24 ml. of ether and 15 ml. of petroleum ether.

Elemental analysis for $C_{22}H_{23}N_3O_8S_2$: Theory: C, 50.66; H, 4.45; N, 8.06. Found: C, 50.41; H, 4.51; N, 7.86.

I.R. (Nujol Mull) carbonyl absorption at 5.65 ($\beta$-lactam) and 5.71 (ester) microns. N.M.R. (DMSO $d_6$). Signals at 7.70 (s, 3H, p-methyl); 6.39 (s, 2H, $C_2$—$H_2$); 4.98 (d, 1H, $C_6$—H); 4.7–4.3 (m, 6H $C_4$—H, ester $CH_2$; $C_3$—$CH_2$, and $C_7$—H); and 2.93–1.68 (m, 8H, aromatic H) tau. U.V. (pH 6 buffer). Maxima at 219 m$\mu$ ($\epsilon$=19,600) and 268 m$\mu$ ($\epsilon$=9,400).

EXAMPLE 3 p-Methoxybenzyl 7-amino-3-methylenecepham-4-carboxylate hydrochloride

To a solution of 4.3 g. of p-methoxybenzyl 7-phenoxyacetamido-3-methylenecepham-4-carboxylate in 50 ml. of methylene chloride were added 880 mg. of dry pyridine and 2.3 g. of phosphorus pentachloride and the mixture was stirred at the reflux temperature for 3 hours. The reaction mixture was then cooled in an ice-water bath and 5 ml. of isobutanol were added. The mixture was stirred in the cold for several hours during which time 2.2 g. of the reaction product, p-methoxybenzyl 7-amino-3-methylenecepham-4-carboxylate hydrochloride, precipitated from the mixture. The product was filtered and washed with cold methylene chloride and was dried in vacuo.

Elemental analysis for $C_{16}H_{19}N_2O_4SCl$: Theory: C, 51.82; H, 5.16; N, 7.55. Found: C, 51.65; H, 5.04; N, 7.72.

EXAMPLE 4 p-Methoxybenzyl 7-amino-3-methylenecepham-4-carboxylate p-toluenesulfonate

To a solution of 937 mg. of p-methoxybenzyl 7-phenoxyacetamido-3-methylenecepham-4-carboxylate in 10 ml. of methylene chloride was added 0.18 ml. of dry pyridine and 460 mg. of phosphorus pentachloride. The mixture was stirred at room temperature for 2 hours and was then cooled to 5°C. To the cold mixture was added 50 ml. of cold methanol and the mixture was allowed to warm to room temperature. The reaction mixture was evaporated in vacuo and the residue was dissolved in a mixture of ethyl acetate and water. The pH of the solution was adjusted to pH 7 and the ethyl acetate layer was separated, washed with water and dried. To the dried ethyl acetate layer was added one equivalent of p-toluene sulfonic acid. On cooling 600 mg. of p-methoxybenzyl 3-methylenecepham-4-carboxylate p-toluenesulfonate precipitated as a crystalline solid.

Elemental analysis for $C_{23}H_{26}N_2O_6S_2$: Theory: C, 54.53; H, 5.17; N, 5.53. Found: C, 54.33; H, 5.05; N, 5.47.

I.R. (Nujol Mull): Carbonyl absorption band at 5.65 ($\beta$-lactam) and 5.78 (ester) microns. N.M.R. (DMSO $d_6$): Signals at 7.69 (s, 3H, para methyl); 6.41 (s, 2H, $C_2$—$H_2$); 6.23 (s, 3H, para methoxy); 5.0 (d, 1H, $C_6$—H); 4.82 (s, 2H, ester $CH_2$); 4.7–4.55 (m, 4H, $C_4$—H, $C_3$—$CH_2$ and $C_7$—H) 3.2–2.0 (m, 8H, aromatic H) tau.

EXAMPLE 5 p-Nitrobenzyl 7-amino-3-hydroxy-3-cephem-4-carboxylate hydrochloride

A solution of 3.85 g. of p-nitrobenzyl 7-amino-3-methylenecepham-4-carboxylate hydrochloride, prepared as described by Example 1, in 600 ml. of methanol was cooled in an acetone-dry ice bath. Ozone was bubbled through the reaction mixture for approximately 20 minutes at which time the reaction mixture developed a faint blue coloration. Nitrogen was then passed through the reaction mixture to expel excess ozone. Next, the intermediate ozonide was decomposed by passing sulfur dioxide gas through the reaction mixture until the mixture gave a negative potassium iodide-starch test.

The reaction mixture was evaporated in vacuo and the residue was dissolved in 200 ml. of 0.1N hydrogen chloride in methylene chloride. The solution was evaporated to dryness and the residual reaction product was dissolved in acetone. On cooling, 3.15 g. of p-nitrobenzyl 7-amino-3-hydroxy-3-cephem-4-carboxylate hydrochloride precipitated as a crystalline solid.

I.R. (Nujol Mull): Carbonyl absorption at; 5.55 ($\beta$-lactam carbonyl) and; 5.02 (ester carbonyl hydrogen bonded to 3 hydroxy) microns. Electrometric titration (66% DMF) pKa 4.0 and 6.3

EXAMPLE 6 p-Nitrobenzyl 7-amino-3-hydroxy-3-cephem-4-carboxylate hydrochloride

A solution of 4 g. of p-nitrobenzyl 7-amino-3-methylenecepham-4-carboxylate hydrochloride in 620 ml. of methanol was cooled in a dry ice-acetone bath and ozone was bubbled through the cold solution for about 20 minutes. The reaction mixture was purged of the remaining ozone by passing nitrogen through the solution and 10 g. of sodium bisulfite were added.

The reaction mixture was stirred for one hour at ice-bath temperature at which time the mixture gave a negative potassium iodide starch test.

The mixture was evaporated in vacuo to yield the reaction product as an amorphous yellow residue. The residue was crystallized in acetone to yield 3.4 g. of p-nitrobenzyl 7-amino-3-hydroxy-3-cephem-4-carboxylate hydrochloride as a crystalline acetone solvate.

I.R. (Nujol Mull): Carbonyl absorption bands at 5.60 ($\beta$-lactam) and 6.04 (ester carbonyl hydrogen bonded to 3 hydroxy) microns.

N.M.R. (DMSO $d_6$): signals at 7.92 (s, 3H, ½ mole acetone); 6.22 (2d, 2H, $C_2$—$H_2$); 5.07 (d, 1H, $C_6H$); 4.8–4.5 (m, 3H, ester $CH_2$ and $C_7H$); 2.4–1.6 (m, 4H, aromatic H) tau.

EXAMPLE 7 p-Nitrobenzyl 7-amino-3-hydroxy-3-cephem-4-carboxylate hydrochloride

Following the ozonization procedure described by Examples 5 and 6, 3.85 g. of p-nitrobenzyl 7-amino-3-methylenecepham-4-carboxylate hydrochloride was ozonized in methanol and the intermediate ozonide was decomposed at a temperature of 0°C. with 3.5 ml. of trimethyl phosphite. The reaction mixture was evaporated and the residue was dissolved in 100 ml. of 0.1N HCl in methylene chloride. The said solution was evaporated and the residue was crystallized from acetone to yield 2.8 g. of p-nitrobenzyl 7-amino-3-hydroxy-3-cephem-4-carboxylate hydrochloride.

EXAMPLE 8 p-Nitrobenzyl 7-amino-3-hydroxy-3-cephem-4-carboxylate

Four millimole of p-nitrobenzyl 7-amino-3-hydroxy-3-cephem-4-carboxylate hydrochloride, prepared as described in Example 5, was dissolved in water and ethyl acetate was added to the solution. The pH of the slurry was adjusted from pH 2.2 to pH 5 with 1N sodium hydroxide. The ethyl acetate layer was separated and was washed with water and dried over magnesium sulfate. The dried ethyl acetate layer was evaporated to dryness to yield 1.2 g. of p-nitrobenzyl 7-amino-3-hydroxy-3-cephem-4-carboxylate as a crystalline residue.

Elemental analysis for: $C_{14}H_{13}N_3O_6S$: Theory: C, 47.86; H, 3.73; N, 11.96. Found: C, 47.87; H, 4.00; N, 12.11.

I.R. (Nujol Mull): Carbonyl absorption at 5.65 (broad, β-lactam and ester) and 6.0 (amide) microns. N.M.R. (DMSO $d_6$): signals at 6.63 (2d, 2H, $C_2H$); 5.31 (d, 1H, $C_6H$); 4.89 (d, 1H, $C_7H$); 4.62 (s, 2H, ester $CH_2$); 4.30 (broad s, 2H, 7 N-H); 2.5–1.8 (m, 4H, aromatic H) and 1.2 (d, 1H, $C_3OH$) tau.

EXAMPLE 9

Methyl 7-phenoxyacetamido-3-hydroxy-3-cephem-4-carboxylate

A solution of 1.6 g. of methyl 7-phenoxyacetamido-3-methylenecepham-4-carboxylate in 300 ml. of methylene chloride was cooled in an acetone-dry ice bath. Ozone was bubbled through the cold solution for three minutes at which time the reaction mixture developed a slight blue coloration. Excess ozone was expelled with a stream of oxygen and 10 g. of sodium bisulfite were added. The reaction mixture was stirred and allowed to warm to 0°C. The liquid phase was separated by decantation and was washed successively with a 5% solution of hydrochloric acid, water and a saturated solution of sodium chloride. The washed mixture was dried and evaporated to yield 1.5 g. of crude methyl 7-phenoxyacetamido-3-hydroxy-3-cephem-4-carboxylate as an amorphous solid.

The crude product was dissolved in ethyl acetate and was extracted with a 5% solution of sodium bicarbonate. Ethyl acetate was added to the extract which was then acidified to pH 2 with 1N hydrochloric acid. The organic phase was separated and washed with a saturated solution of sodium chloride and dried. The dried extract was evaporated to dryness to yield 709 mg. of the reaction product contaminated with a minor amount of the corresponding 3-hydroxy-3-cephem sulfoxide, an over oxidation product. The product was separated from the sulfoxide impurity and obtained pure by preparative thin layer chromatography on silica gel with chloroform:methanol (9:1).

Elemental analysis for: $C_{16}H_{16}N_2O_6S\cdot H_2O$ Theory: C, 50.26; H, 4.75; N, 7.33; S, 8.38. Found: C, 51.03; H, 4.62; N, 7.06; S, 8.37.

I.R. (chloroform): absorption peaks at 2.8 (amide NH), 5.6 (β-lactam carbonyl), 5.85 (broad, amide and ester carbonyl and 6.6 (amide II) microns. N.M.R. (CDCl$_3$): signals at 6.65 (s, 2H, $C_2$—$H_2$), 6.13 (s, 3H, methyl ester), 5.40 (s, 2H, side-chain $CH_2$), 4.93 (d, 1H, $C_6H$), 4.32 (q, 1H, $C_7H$), 3.15–2.38 (m, 6H, aromatic and amide H), and 1.60 (broad s, 1H, 3—OH) tau. Electrometric titration (66% aqueous DMF): pKa 5.6.

EXAMPLE 10 p-Methoxybenzyl 7-phenoxyacetamido-3-hydroxy-3-cephem-4-carboxylate

A solution of 2.5 g. of p-methoxybenzyl 7-phenoxyacetamido-3-methylenecepham-4-carboxylate in 350 ml. of ethyl acetate was cooled in an acetone-dry ice bath. Ozone was bubbled through the cold solution for 8 minutes and then oxygen was passed through the ozonized reaction mixture to expel excess ozone. The intermediate ozonide was decomposed by adding to the reaction mixture 25 g. of sodium bisulfite with stirring at a temperature of about 0°C. The reaction solution was decanted and was washed successively with water, 5% hydrochloric acid and a saturated solution of sodium chloride. The washed mixture was dried and evaporated to yield the reaction product, p-methoxybenzyl 7-phenoxyacetamido-3-hydroxy-3-cephem-4-carboxylate as an amorphous solid.

N.M.R. (CDCl$_3$): signals at 6.73 (s, 2H, $C_2H_2$), 6.23 (s, 3H, p-methoxy), 5.53 (s, 2H, side-chain $CH_2$), 5.03 (d, 1H, $C_6H$), 4.87 (s, 2H, ester $CH_2$), 4.47 (q, 1H, $C_7H$), 3.40–2.50 (m, 9H, aromatic H), 2.33 (d, 1H, amide NH), and 1.53 (broad s, 1H, 3 OH) tau.

EXAMPLE 11 p-Nitrobenzyl 7-[2-(2-thienyl)acetamido]-3-hydroxy-3-cephem-4-carboxylate

To a solution of 1.55 g. of p-nitrobenzyl 7-amino-3-hydroxy-3-cephem-4-carboxylate hydrochloride in 30 ml. of acetone containing 364 mg. (0.5 ml., 3.6 mmole) of triethylamine was added 962 mg. of urea. With stirring at room temperature, a solution of 730 mg. (4.4 mmole) of 2-thiophene acetyl chloride in 20 ml. of acetone was added dropwise to the mixture. After 2.5 hours the reaction mixture was filtered and evaporated. The residue was dissolved in ethyl acetate and the solution was washed successively with water, a 5% solution of sodium bicarbonate, 5% hydrochloric acid, and a saturated solution of sodium chloride. The washed solution was dried and then was concentrated by evaporation in vacuo to yield 1.2 g. of the reaction product as a crystalline residue. The product was recrystallized from ethyl acetate to yield pure p-nitrobenzyl 7-[2-(2-thienyl)acetamido]-3-hydroxy-3-cephem-4-carboxylate having the following spectral properties.

I.R. (Nujol Mull): absorption peaks at 3.0 (amide NH), 5.68 (β-lactam carbonyl), and 6.1 (amide, and ester hydrogen bonded to 3 OH) microns.

N.M.R. (CDCl$_3$DMSO $d_6$): signals at 6.54 (2d, 2H, $C_2H_2$), 6.16 (s, 2H, side-chain $CH_2$), 4.90 (d, 1H, $C_6H$) 4.60 (d, 2H, ester $CH_2$), 4.43 (q, 1H, $C_7H$), 3.1–1.6 (m, 7H, aromatic H) and 1.30 (d, 1H, amide NH) tau.

EXAMPLE 12 p-Nitrobenzyl 7-[2-(2-thienyl)acetamido]-3-hydroxy-3-cephem-4-carboxylate p-Nitrobenzyl 7-amino-3-methylenecepham-4-carboxylate hydrochloride, 3.85 g., was reacted with ozone in methanol as described in Example 5 to provide the ozonide. The ozonide was decomposed with sulfur dioxide to produce the 3-hydroxy product which was isolated as crude product. The crude 3-hydroxy-3- cephem nucleus ester was dissolved in 175 ml. of tetrahydrofuran and 50 ml. of water. Sodium bisulfite, 2.1 g., was suspended in the solution and a solution of 4.8 g. of 2-thiophene acetyl chloride in 200 ml. of THF was added dropwise to the suspension.

The mixture was stirred for 2 hours at room temperature and was then evaporated to an aqueous residue. The residue was slurried with ethyl acetate, the organic layer separated and washed with 5% hydrochloric acid and with water. The washed layer was dried and evaporated to dryness to yield the reaction product as a crystalline residue. The residue was triturated three times with diethyl ether to remove contaminating 2-thiophene acetic acid and to provide 2.9 g. of the purified crystalline product, p-nitrobenzyl 7-[2-(2-thienyl)acetamido]-3-hydroxy-3-cephem-4-carboxylate.

Electrometric titration (66% aqueous DMF) pKa 5.9.

N.M.R. ($CDCl_3/D_2O$): signals at 6.60 (s, 2H, $C_2H_2$), 6.13 (s, 2H, side-chain $CH_2$), 4.96 (d, 1H, $C_6H$), 4.62 (d, 2H, ester $CH_2$), 4.46 (d, 1H, $C_7H$) and 3.1–1.7 (m, 7H, aromatic H) tau.

EXAMPLE 13 p-Nitrobenzyl 7-acetamido-3-hydroxy-3-cephem-4-carboxylate

A solution of 10 mmole of p-nitrobenzyl 7-amino-3-hydroxy-3-cephem-4-carboxylate hydrochloride in a mixture of 325 ml. of acetone and 125 ml. of water was cooled in an ice-water bath. With stirring a stream of ketene gas was bubbled through the solution for 30 minutes. Thereafter the reaction mixture was evaporated to remove acetone and the aqueous residue was slurried with ethyl acetate. The ethyl acetate layer was separated and was washed with 5% hydrochloric acid and a saturated solution of sodium chloride. The washed extract was dried and evaporated in vacuo to yield the reaction product as a crystalline residue. The residue was triturated with diethyl ether and vacuum dried to yield 3.55 g. of p-nitrobenzyl 7-acetamido-3-hydroxy-3-cephem-4-carboxylate melting at about 146°–152°C. with decomposition.

Elemental analysis for: $C_{16}H_{15}N_3O_7S$: Theory: C, 48.85; H, 3.84; N, 10.68. Found: C, 48.97; H, 3.96; N, 10.42.

I.R. ($CHCl_3$): absorption bands at 2.9 and 3.0 (amide NH and OH), 5.63 ($\beta$-lactam carbonyl) and 5.95 (broad, amide, and ester carbonyl hydrogen bonded to 3 OH) microns.

N.M.R. ($CDCl_3$): signals at 7.90 (s, 3H, 7-acetamido $CH_3$), 6.55 (s, 2H, $C_2H_2$), 4.92 (d, 1H, $C_6H$), 4.63 (m, 2H, ester $CH_2$), 4.30 (q, 1H, $C_7H$), 2.81 (d, 1H, amide NH), 2.5–1.8 (m, 4H, aromatic H), and 2.8 (s, 1H, $C_3OH$) tau.

Electrometric titration (66% aqueous DMF) pKa 5.9

EXAMPLE 14 p-Nitrobenzyl 7-phenylacetamido-3-hydroxy-3-cephem-4-carboxylate

Following the ozonization procedures described in Example 9, a solution of 350 mg. of p-nitrobenzyl 7-phenylacetamido-3-methylenecepham-4-carboxylate in 250 ml. of methylene chloride was cooled to −78°C. and was ozonized. The intermediate ozonide was decomposed in situ with sulfur dioxide and the reaction product was recovered and obtained crystalline by extraction with ethyl acetate.

Elemental analysis for $C_{22}H_{19}N_3O_7S$: Theory: C, 56.28; H, 4.80; N, 8.95. Found: C, 56.11; H, 4.15; N, 8.74.

N.M.R. ($CDCl_3$): signals at 6.68 (2d, 2H, $C_2H_2$), 6.37 (s, 2H, side-chain $CH_2$), 5.03 (d, 1H, $C_6H$), 6.66 (d, 2H, ester $CH_2$), 4.40 (q, 1H, $C_7H$), 2.7 (m, 6H, amide NH and aromatic H), 2.53–1.70 (q, 4H, aromatic H) and a singlet in low field integrating for 1H of $C_3$ hydroxyl group tau.

I.R. (Nujol Mull): absorption peaks at 3.04 (amide), 5.60 and 6.0 ($\beta$-lactam, ester and amide carbonyls) microns.

EXAMPLE 15 p-Nitrobenzyl 7-(D-$\alpha$-phenyl-$\alpha$-formyloxyacetamido)-3-hydroxy-3-cephem-4-carboxylate To a solution of 1.54 g. of p-nitrobenzyl 7-amino-3-hydroxy-3-cephem-4-carboxylate hydrochloride in 120 ml. of acetone and 40 ml. of water was added 936 mg. of sodium bisulfite. With stirring a solution of 960 mg. of O-formyl-D-mandelic acid chloride in 20 ml. of anhydrous acetone was added dropwise at room temperature. The reaction mixture was stirred at room temperature for 16 hours and was then evaporated to remove acetone. The aqueous residue was slurried with ethyl acetate and the organic layer separated. The extract was washed with water was dried and evaporated. The crystalline residue was triturated with diethyl ether and dried to yield 1 g. of p-nitrobenzyl 7-(D-$\alpha$-phenyl-$\alpha$-formyloxyacetamido)-3-hydroxy-3-cephem-4-carboxylate.

Elemental analysis for $C_{23}H_{19}N_3O_9S$: Theory: C, 53.80; H, 3.73; N, 8.18. Found: C, 53.51; H, 3.81; N, 8.46.

I.R. ($CHCl_3$): carbonyl absorption peaks at 5.55, 5.73, 5.85 and 5.93 microns.

N.M.R. ($CDCl_3$): signals at 6.61 (s, 2H, $C_2H_2$), 4.95 (d, 1H, $C_6H$), 4.61 (d, 2H, ester $CH_2$), 4.39 (q, 1H, $C_7H$), 3.70 (s, 1H, $\alpha$—CH), and 2.80–1.70 (m, 11H, amide NH and aromatic H) tau.

B. Preparation of 3-halo-3-cephem acids and esters.

EXAMPLE 16

Diphenylmethyl 7-[2-(2-thienyl)acetamido]-3-chloro-3-cephem-4-carboxylate a. To a solution of 34 g. (100 mmole) of 7-[2-(2-thienyl)acetamido]-3-methylenecepham-4-carboxylic acid in 500 ml. of methylene chloride was added 21.4 g. (110 mmole) of diphenyl diazomethane and the resulting mixture was stirred for 2 hours at room temperature. The solvent was evaporated under reduced pressure and the residue was dissolved in ethyl acetate. The ethyl acetate solution was washed with a 5% solution of sodium bicarbonate, then with water and was dried over magnesium sulfate. The dried solution was concentrated to a small volume. On standing 40 g. of diphenylmethyl 7-[2-(2-thienyl)acetamido]-3-methylenecepham-4-carboxylate melting at about 132°–133°C. precipitated as a crystalline solid.

IR (chloroform): absorption peaks at 2.9 (amide N—H), 5.65, 5.75 and 5.93 ($\beta$-lactam, ester and amide carbonyls respectively) and 6.62 (amide II) microns.

NMR (CDCl$_3$): signals at 6.72 (ABq, 2H, C$_2$—H$_2$), 6.21 (s, 2H, α-CH$_2$), 4.83–4.65 (m, 4H, C$_4$—H, C$_6$—H and C$_3$—CH$_2$), 4.39 (q, 1H, C$_7$—H), 3.4–2.65 (m, 15H, C$_7$—NH, ester CH and aromatic H) tau.

b. To the solution of 8.1 g. (16 mmole) of the above ester in 80 ml. of methylene chloride were added 1.57 g. (1.6 ml, 19.6 mmole) of dry pyridine and 3.8 g. (18.1 mmole) of phosphorus pentachloride. The reaction mixture was stirred for 2 hours at room temperature and was thereafter cooled in an ice-water bath. The cold mixture was treated with 8 ml. of isobutanol with stirring. Stirring was continued for 2 hours during which time 3 g. of diphenylmethyl 7-amino-3-methylenecepham-4-carboxylate hydrochloride formed as a crystalline precipitate. The product was filtered and washed with methylene chloride and vacuum dried.

Elemental analysis (percent) for C$_{21}$H$_{21}$N$_2$O$_3$SCl: Theory: C, 60.50; H, 5.08; N, 6.72; Cl, 8.50; Found: C, 60.70; H, 5.02; N, 6.71; Cl, 8.80.

NMR (DMSO d$_6$): signals at 6.45 (ABq, 2H, C$_2$—H$_2$), 5.00 (d, 1H, C$_6$—H), 4.68 (d, 1H, C$_7$—H), 4.60 (s, 2H, 3—CH$_2$), 4.44 (s, 1H, C$_4$—H), 3.10 (s, 1H, ester CH), and 2.61 (s, 10H, aromatic H) tau.

c. The 7-amino-3-exomethylenecepham ester hydrochloride salt product, 2.1 g. (5 mmole) was dissolved in 200 ml. of methanol and the solution was cooled in an acetone-dry ice bath. Ozone was bubbled into the cold solution for 7 minutes to form the intermediate ozonide. The ozonide was decomposed by passing a stream of sulfur dioxide gas through the reaction mixture for 2 minutes. Thereafter the reaction mixture was evaporated and the residue was triturated with diethyl ether to yield 1.6 g. of diphenylmethyl 7-amino-3-hydroxy-3-cephem-4-carboxylate hydrochloride as a crystalline solid.

NMR (CDCl$_3$): signals at 6.4 (ABq, 2H, C$_2$–H$_2$), 5.0–4.5 (m, 2H, C$_6$—H and C$_7$—H), 3.2–2.4 (m, 11H, ester CH and aromatic H) tau.

IR (chloroform): carbonyl absorption peaks at 5.57 and 5.70 (β-lactam and ester carbonyl respectively) microns UV (pH7 buffer): λ max 275 mμ, ε=7550.

Electrometric titration (60% aq. DMF): titratable groups at 4.5 and 6.5.

d. To a solution of 840 mg. of diphenylmethyl 7-amino-3-hydroxy-3-cephem-4-carboxylate in 10 ml. of water and 10 ml. of acetone was added one gram of sodium bisulfite. The mixture was stirred and 800 mg. of thiophene-2-acetyl chloride in 10 ml. of acetone were added dropwise. The mixture was stirred for 4.5 hours at room temperature and was then evaporated under reduced pressure. The residue was dissolved in a mixture of ethyl acetate and an aqueous 5% solution of sodium bicarbonate. The ethyl acetate layer was separated, washed with water and dried. The dried solution was evaporated and the residue triturated with ether to yield 500 mg. of diphenylmethyl 7-[2-(2-thienyl)acetamido]-3-hydroxy-3-cephem-4-carboxylate.

NMR (CDCl$_3$): signals at 6.79 (s, 2H, C$_2$—H$_2$), 6.16 (s, 2H, α-CH$_2$), 5.0 (d, 1H, C$_7$—H), 4.32 (q, 1H, C$_7$—H), 3.05–2.46 (m, 15H, C$_7$—NH, ester CH and aromatic H) tau.

I.R. (chloroform): absorption peaks at 2.9 (amide NH), 5.6, 5.73 and 5.95 (β-lactam, ester and amide carbonyls respectively) and 6.65 (amide II) microns.

e. To a solution of 4.2 g. of diphenylmethyl 7-[2-(2-thienyl)acetamido]-3-hydroxy-3-cephem-4-carboxylate in 44 ml. of dry dimethylformamide was added 865 mg. of phosphorus trichloride. The mixture was stirred for 1.5 hours at room temperature and was poured into an ethyl acetate 5% aqueous hydrochloric acid mixture. The ethyl acetate layer was evaporated, was washed with 5% hydrochloric acid, water and was dried. The dried solution was concentrated in vacuo and the product crystallized. The 3-chloro ester was filtered, washed with cold ethyl acetate and dried to yield 2.2 g.

Elemental analysis (percent) for C$_{26}$H$_{21}$N$_2$O$_4$S$_2$Cl: Theory: C, 59.48; H, 4.03; N, 5.34; Cl, 6.75. Found: C, 59.77, H, 4.25; N, 5.40; Cl, 6.91.

NMR (CDCl$_3$): signals at 6.49 (ABq, 2H, C$_2$—H$_2$), 6.22 (s, 2H, α-CH$_2$), 5.08 (d, 1H, C$_6$—H), 4.19 (q, 1H, C$_7$—H), 3.13–2.5 (m, 15H, C$_7$—NH, ester CH, and aromatic H) tau.

I.R. (CHCl$_3$): absorption peaks at 2.9 (amide NH), 5.55, 5.72 and 5.90 (β-lactam, ester and amide carbonyls) and 6.60 (amide II) microns.

U.V. (dioxane): λ max 275 mμ, ε=8700.

EXAMPLE 17 p-Nitrobenzyl 7-[2-(2-thienyl)acetamido]-3-chloro-3-cephem-4-carboxylate (via thionyl chloride).

To a solution of 1.9 g. (4 mmole) of p-nitrobenzyl 7-[2-(2-thienyl)acetamido]-3-hydroxy-3-cephem-4-carboxylate in 10 ml. of DMF (dried over a molecular sieve) was added 950 mg. (0.58 ml., 8 mmole) of freshly distilled thionyl chloride. The mixture was stirred at room temperature for 6.5 hours and was then poured into 100 ml. of ethyl acetate. The mixture was extracted three times with 30 ml. portions of 5% hydrochloric acid and with a saturated solution of sodium chloride. The washed ethyl acetate solution was filtered and evaporated to dryness in vacuo. The residue was triturated with ether to yield 1.2 g. of p-nitrobenzyl 7-[2-(2-thienyl)acetamido]-3-chloro-3-cephem-4-carboxylate as a brown crystalline solid melting at about 164°–166°C.

Elemental analysis (percent) for C$_{20}$H$_{16}$N$_3$O$_6$S$_2$Cl: Theory: C, 48.63; H, 3.27; N, 8.51; Cl, 7.18. Found: C, 48.47; H, 3.29; N, 8.78; Cl, 6.96.

IR (Chloroform) showed absorption bands at 2.9 (amide NH), 5.59 (β-lactam carbonyl), 5.75 (ester carbonyl) and 5.92 microns (amide carbonyl). UV absorption spectrum (acetonitrile) showed maxima at λ max 235 mμ, ε = 12,100; and λ max 268 mμ, ε = 15,800.

The mass spectrum of the product showed a molecular ion of 493 m/e.

NMR (CDCl$_3$) showed signals at 6.39 (ABq, 2H, C$_2$—H$_2$), 6.17 (s, 2H, α—CH$_2$), 4.99 (d, 1H, C$_6$—H), 4.64 (s, 2H, ester CH$_2$), 4.19 (q, 1H, C$_7$—H), 3.45 (d, 1H, C$_7$—NH), 3.1–1.67 (m, 7H, aromatic H) tau.

EXAMPLE 18

7-[2-(2-Thienyl)acetamido]-3-chloro-3-cephem-4-carboxylic acid.

To a solution of 995 mg. (2 mmole) of p-nitrobenzyl 7-[2-(2-thienyl)acetamido]-3-chloro-3-cephem-4-carboxylate, prepared as described in Example 17, in 60 ml. of tetrahydrofuran and 100 ml. of methanol containing 5 drops of 1N hydrochloric acid was added one gram of 5% palladium on carbon catalyst. The catalyst was prereduced as a suspension in 40 ml. of ethanol at room temperature under 50 psi hydrogen pressure prior to use.

The suspension was hydrogenated at room temperature for 2.5 hours under a hydrogen pressure of 50 psi. The catalyst was filtered and washed on the filter with THF and with water. The combined filtrate and catalyst washes were evaporated to dryness and the reaction product residue was dissolved in a mixture of ethyl acetate and water. The pH of the solution was adjusted to pH 2.5 and the ethyl acetate layer was separated. The acid reaction product was extracted with water from the ethyl acetate solution at pH 7. The aqueous phase was separated, layered with ethyl acetate and acidified to pH 2.5. The ethyl acetate layer was separated, washed with water, dried over sodium sulfate and dried in vacuo. The amorphous residue was triturated with ether to yield 165 mg. of 7-[2-(2-thienyl)acetamido]-3-chloro-3-cephem-4-carboxylic acid as a crystalline solid melting at about 114°–120°C. with decomposition and softening at about 110°C.

The reduction product had the following physical characteristics.

I.R. (nujol mull) showed absorption bands at 3.1 (amide NH), 5.64 and 5.75 (β-lactam and carboxylic acid carbonyls respectively) and 6.1 (amide II) microns.

U.V. (acetonitrile): absorption maxima at λ max 235, ε = 10,700; λ max 268, ε = 7,200. NMR (CDCl$_3$) shows signals at 6.38 (ABq, 2H, C$_2$-H$_2$), 6.16 (s, 2H, α-CH$_2$), 4.98 (d, 1H, C$_6$-H), 4.20 (q, 1H, C$_7$-H) and 3.1–2.5 (m, 4H, aromatic H and C$_7$—NH) tau. Percent Elemental Composition for C$_{13}$H$_{11}$N$_2$O$_4$SCl Theory: C, 43.52; H, 3.09; N, 7.81; Cl, 9.88. Found: C, 43.55; H, 3.79; N, 7.27; Cl, 9.28.

EXAMPLE 19 p-Nitrobenzyl 7-[2-(2-Thienyl)acetamido]-3-chloro-3-cephem-4-carboxylate (via phosphorus trichloride).

To a cooled solution of 439 mg. (0.93 mmole) of p-nitrobenzyl 7-[2-(2-thienyl)acetamido]-3-hydroxy-3-cephem-4-carboxylate in 4.4 ml. of DMF was slowly added 85 mg. (0.05 ml., 0.63 mmole) of phosphorus trichloride. The reaction mixture was allowed to stand for 4 hours at room temperature and thereafter the reaction product mixture was worked-up by following the recovery procedures described in Example 19 to provide 374 mg. of p-nitrobenzyl 7-[2-(2-thienyl)acetamido]-3-chloro-3-cephem-4-carboxylate. The NMR spectrum of the product was consistent with the expected product and with that of the compound of Example 17.

EXAMPLE 20

7-Phenoxyacetamido-3-chloro-3-cephem-4-carboxylic acid.

Following the chlorination procedure of Example 19 p-nitrobenzyl 7-phenoxyacetamido-3-chloro-3-cephem-4-carboxylate was prepared with phosphorus trichloride. The p-nitrobenzyl ester group was removed by the acidic hydrogenolysis procedure described by Example 18 to provide the 3-chlorocephalosporanic acid antibiotic compound.

EXAMPLE 21 p-Nitrobenzyl 7-[2-(2-thienyl)acetamido]-3-chloro-3-cephem-4-carboxylate (via phosphorus oxychloride).

To a solution of 325 mg. (0.7 mmole) of p-nitrobenzyl 7-[2-(2-thienyl)acetamido]-3-hydroxy-3-cephem-4-carboxylate in 3.3 ml. of DMF cooled in an ice-water bath, was slowly added 212 mg. (0.13 ml., 1.4 mmole). The mixture was allowed to stand for 4 hours at room temperature and 225 mg. of the product was recovered by following the work-up procedures described in Example 17. The nuclear magnetic resonance spectrum of the product was consistent with the spectrum of the previously characterized compound.

EXAMPLE 22 p-Nitrobenzyl 7-[2-(2-thienyl)acetamido]-3-chloro-3-cephem-4-carboxylate (via oxalyl chloride).

To a solution of 439 mg. (0.93 mmole) of p-nitrobenzyl 7-[2-(2-thienyl)acetamido]-3-hydroxy-3-cephem-4-carboxylate in 4.4 ml. of DMF cooled in an ice bath was added dropwise 118 mg. (0.07 ml., 0.93 mmole) of oxalyl chloride. The reaction mixture was allowed to stand for 4 hours at room temperature and was then poured into a mixture of aqueous 5% hydrochloric acid and ethyl acetate. The organic layer was separated and was washed sequentially with 5% hydrochloric acid, water and a saturated solution of sodium chloride. The washed layer was dried and evaporated to dryness to yield the reaction product, p-nitrobenzyl 7-[2-(2-thienyl)acetamido]-3-chloro-3-cephem-4-carboxylate as an amorphous solid. The product was obtained crystalline by triturating the amorphous residue with ether. Yield 350 mg. The infrared spectrum and NMR spectrum of the crystalline product were consistent with the spectra of authentic material.

EXAMPLE 23

7-[2-(2-Thienyl)acetamido]-3-bromo-3-cephem-4-carboxylic acid.

To a solution of 19 g. (40 mmole) of p-nitrobenzyl 7-[2-(2-thienyl)acetamido]-2-hydroxy-3-cephem-4-carboxylate in 300 ml of dry DMF was added 15 g. (56 mmole) of phosphorus tribromide and the reaction mixture was stirred at room temperature overnight. The reaction mixture was poured into a mixture of ethyl acetate and water and the organic phase was separated and washed repeatedly with water and dried over magnesium sulfate. The dried organic phase was evaporated in vacuo to dryness. The crude reaction product residue weighing about 9 g. was purified by chromatography over 500 g. of silica gel using ethyl acetate-hexane (55:45 v:v) as eluent. The eluate was evaporated to dryness under reduced pressure and the product, p-nitrobenzyl 7-[2-(2-thienyl)acetamido]-3-bromo-3-cephem-4-carboxylate was obtained crystalline by triturating the dry residue with diethyl ether.

U.V. (ethanol) λ max, 270 mμ (ε=13,300); and λ max. 243 mμ (ε=12,700) Elemental analysis calculated for C$_{20}$H$_{16}$BrN$_3$O$_6$S$_2$: Theory: C, 44.61; H, 3.00; N, 7.81; Br, 14.84. Found: C, 44.78; H, 3.03; N, 7.65; Br, 14.91.

Nuclear magnetic resonance spectrum (DMSO d6) showed signals at 6.21 (s, 2H, α—CH$_2$), 5.98 (ABq, 2H, C$_2$—H$_2$), 4.72 (d, 1H, C$_6$—H), 451 (s, 2H, ester—CH$_2$), 420 (q, 1H, C$_7$—H), 3.04–1.74 (m, 7H; aromatic H) and 0.66 (d, 1H, C$_7$—CH) tau.

The above 3-bromo ester was de-esterified in the following manner. The ester, 545 mg. (1.0 mmole) was hydrogenated at room temperature in ethanol in the presence of pre-reduced 5 percent palladium-on-carbon catalyst. The catalyst was filtered and the filtrate evaporated under reduced pressure to dryness. The residual product was triturated with diethyl ether to yield 180 mg. (44 percent) of crystalline product, 7-[2-(2-thienyl)acetamido]-3-bromo-3-cephem-4-carboxylic acid.

Electrometric titration (66 percent aqueous DMF) showed a pKa of 4.4 and an apparent molecular weight of 393. The calculated molecular weight = 403. Elemental analysis calculated for C$_{13}$H$_{11}$BrN$_2$O$_4$S$_2$. ½ diethyl etherate: Theory: C, 40.91; H, 3.66; N, 6.36; Br, 18.15. Found: C, 41.29; H, 3.20; N, 6.29; Br, 18.50.

Nuclear magnetic resonance spectrum (CDCl$_3$) showed signals at 8.8 (t, diethyl ether-CH$_3$), 6.68–5.86 (m, C$_2$—H$_2$, α—CH$_2$ and diethyl ether-CH$_2$), 4.90 (d, 1H, C$_6$—H), 3.0–2.63 (m, 3H, aromatic—H), and 1.9 (d, 1H, amide NH) tau.

EXAMPLE 24

Following the bromination method of Example 23, p-nitrobenzyl 7-phenoxyacetamido-3-bromo-3-cephem-4-carboxylate is prepared with phosphorus tribromide.

EXAMPLE 25

Following the bromination method of Example 23, 2,2,2-trichloroethyl 7-acetamido-3-bromo-3-cephem-4-carboxylate is prepared with phosphorus tribromide.

EXAMPLE 26

7-[2-(2-Thienyl)acetamido]-3-fluoro-3-cephem-4-carboxylic acid.

To a solution of 325 mg. (0.7 mmole) of p-nitrobenzyl 7-[2-(2-thienyl)acetamido]-3-hydroxy-3-cephem-4-carboxylate in 10 ml. of methylene chloride was slowly added an equivalent amount of N-(2-chloro-1,1,2-trifluoroethyl) diethylamine. The reaction mixture was heated for 30 minutes under gentle reflux and was then evaporated to dryness in vacuo. The residue was dissolved in a mixture of ethyl acetate-water and the organic layer was separated. The organic layer was washed with 5% hydrochloric acid, water and brine and was then dried. The dried reaction product solution was concentrated to a small volume and n-hexane was added to precipitate, p-nitrobenzyl 7-[2-(2-thienyl)acetamido]-3-fluoro-3-cephem-4-carboxylate.

The ester group was removed by catalytic hydrogenolysis by the method described in Example 18 to yield the 3-fluoro cephalosporin free acid antibiotic.

EXAMPLE 27

7-[2-(2-Thienyl)acetamido]-3-fluoro-3-cephem-4-carboxylic acid.

To a solution of 4.75 g. (10 mmole) of p-nitrobenzyl 7-[2-(2-thienyl acetamido]-3-hydroxy-3-cephem-4-carboxylate in 50 ml. of dry N,N-dimethylacetamide were added 2 ml. of propylene oxide. To the solution was added with stirring one equivalent of methanesulfonyl chloride, and stirring was continued for 3 hours. The reaction mixture was then taken up in ethyl acetate, and the solution was washed with a saturated solution of sodium chloride. The washed organic phase was evaporated in vacuo to dryness to obtain the reaction product mixture as a residue. The reaction product was purified by preparative thin layer chromatography on silica gel using for preparative thin layer chromatography on silica gel using for elution 65 percent ethyl acetate/hexane.

The purified product gave the following percent elemental composition on microanalysis.

Calculated for C$_{21}$H$_{19}$N$_3$O$_9$S$_3$ Theory: C, 45.56; H, 3.46; N, 7.59; S, 17.38. Found: C, 45.74; H, 3.56; N, 7.30; S, 17.06.

The nuclear magnetic resonance spectrum and the infrared absorption spectrum were in agreement with the structure of the title compound.

To 93 mg. of dicyclohexyl-18-crown-6 ether in 15 ml. of acetonitrile (dried over molecular sieves) were added 25 mg. of potassium fluoride which had been dried in vacuo at 90°C. The mixture was stirred for ten minutes, and 138 mg. of p-nitrobenzyl 7-[2-(2-thienyl)acetamido]-3-methylsulfonyloxy-3-cephem-4-carboxylate in 4 ml. of acetonitrile were then added. The mixture was stirred for 1 hour. The mixture was acidified by addition of dilute (5%) HCl, and the resulting acidified mixture was extracted with ethyl acetate. Pure product was obtained from the ethyl acetate extract by preparative thin layer chromatogrphy on silica gel using ethyl acetate:benzene (1:1). Ten mg. of p-nitrobenzyl 7-[2-(2-thienyl)acetamido]-3-fluoro-3-cephem-4-carboxylate were obtained.

I.R.: absorption peaks at 1792, 1740, and 1685 cm.$^{-1}$ NMR (CDCl$_3$) showed signals at 6.15 (s, 2H, α-CH$_2$), 4.97 (d, 1H, J=4Hz, C$_6$—H), 4.20 (q, 1H, C$_7$—H), 3.52 (d, 1H, C$_7$-NH), 2.32–1.7 (m, 2H, C$_2$-H$_2$) tau. Fluorine NMR — (d, J=10 Hz). M.S.: calculated — 477.0465. found — 477.0455.

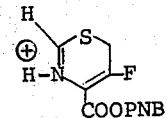

Fragment calculated — 297.0345. found — 297.0344.

To 110 ml. of methanol and 83 mg. of pre-reduced 5 percent palladium on carbon were added 83 mg. of p-nitrobenzyl 7-[2-(2-thienyl)acetamido]-3-fluoro-3-cephem-4-carboxylate. The mixture was hydrogenated at 53 psig. for one hour. The resulting mixture was filtered, the filtered catalyst was washed with methanol, and the methanol washings were added to the filtrate. The filtrate was then evaporated in vacuo. The residue was dissolved in ethyl acetate, and the ethyl acetate solution was extracted with dilute aqueous sodium bicarbonate. The sodium bicarbonate solution was washed with ethyl acetate, layered with ethyl acetate, and dilute aqueous HCl was added. The layered ethyl acetate was separated and evaporated to recover 7-[2-(2-thienyl)acetamido]-3-fluoro-3-cephem-4-carboxylic acid, shown by bioautogram to be biologically active.

EXAMPLE 28 p-Nitrobenzyl 7-amino-3-chloro-3-cephem-4-carboxylate hydrochloride.

To a solution of 500 mg. of p-nitrobenzyl 7-[2-(2-thienyl)acetamido]-3-chloro-3-cephem-4-carboxylate in 6 ml. of methylene chloride was added 95 mg. of dry pyridine and 237 mg. of phosphorus pentachloride. The reaction mixture was stirred at room temperature for 1.5 hours, was thereafter cooled in an ice-water bath to about 5°C. and 0.6 ml. of isobutyl alcohol were added. On continued cooling and stirring the reaction product, p-nitrobenzyl 7-amino-3-chloro-3-cephem-4-carboxylate hydrochloride, crystallized from the reaction mixture. The product was filtered, washed with cold methylene chloride and dried to yield 200 mg. of the crystalline product melting with decomposition at about 168°C.

Percent elemental composition for $C_{14}H_{13}ClN_3O_5S \cdot HCl$: Theory: C, 41.39; H, 3.20; N, 10.34; Cl, 17.45. Found: C, 41.14; H, 3.31; N, 10.44; Cl, 17.29. I.R. (nujol mull): showed absorption bands at 5.55 ($\beta$-lactam carbonyl) and; at 5.78 (ester carbonyl) microns.

UV (pH 7 buffer): showed absorption maximum $\lambda$ max 268 m$\mu$ ($\epsilon$ = 13,800) N.M.R. (DMSO $d_6$): signals at 5.97 (s, 2H, $C_2$—$H_2$), 4.8–4.5 (m, 4H, $C_6$—H, $C_7$—H and ester $CH_2$), and 2.35–1.6 (q, 4H, aromatic H) tau.

The free base of the above nucleus ester hydrochloride salt, namely, p-nitrobenzyl 7-amino-3-chloro-3-cephem-4-carboxylate, gave the following percent elemental composition on elemental analysis:

Calculated for $C_{14}H_{12}ClN_3O_5S$: Theory: C, 45.47; H, 3.27; N, 31, 9.59. Found: C, 45.20; H, 3.48; N, Cl, 9.61.

EXAMPLE 29

7-Amino-3-chloro-3-cephem-4-carboxylic acid.

To a solution of 750 mg. (1.85 mmole) of p-nitrobenzyl 7-amino-3-chloro-3-cephem-4-carboxylate hydrochloride in 20 ml. of tetrahydrofuran and 40 ml. of methanol was added a suspension of 750 mg. of prereduced 5% palladium on carbon catalyst in 20 ml. of ethanol and the suspension was hydrogenated under 50 psi of hydrogen at room temperature for 45 minutes. The catalyst was filtered and washed with THF and water. The filtrate and catalyst washes were combined and evaporated to dryness. The residue was dissolved in a water-ethyl acetate mixture and the pH adjusted to pH 3. The insoluble product was filtered and triturated with acetone. The product was then dried to yield 115 mg. of 7-amino-3-chloro-3-cephem-4-carboxylic acid.

I.R. mull): absorption peaks at 5.61 ($\beta$-lactam carbonyl), and 6.2 (carboxylic acid).

NMR ($D_2O$-$NaHCO_3$): signals at 6.25 (ABq, 2H, $C_2$—$H_2$) 4.88 (d, 1H, $C_6$—H) and 4.54 (d, 1H, $C_7$—H) tau.

U.V. (pH 7 buffer): absorption maximum at $\lambda$ max 265 m$\mu$, $\epsilon$ = 7550.

EXAMPLE 30

Diphenylmethyl 7-amino-3-chloro-3-cephem-4-carboxylate.

To a solution of 525 mg. of diphenylmethyl 7-[2-(2-thienyl)acetamido]-3-chloro-3-cephem-4-carboxylate in 20 ml. of methylene chloride was added 0.1 ml. of dry pyridine and 237 mg. of phosphorus pentachloride. The reaction mixture was stirred for 2 hours at room temperature and was then cooled in an ice-water mixture. To the cold mixture was added 0.6 ml. of isobutanol and after 30 minutes the reaction mixture was evaporated. The residue was dissolved in ethyl acetate and the solution was washed with 5% sodium bicarbonate and with water and was dried. The dried solution was evaporated to dryness and the residue was triturated with ether to yield 190 mg. of 3-chloro nucleus ester, diphenylmethyl 7-amino-3-chloro-3-cephem-4-carboxylate.

I.R. (mull): absorption peaks at 5.7 and 5.9 ($\beta$-lactam and ester carbonyl) microns.

NMR ($CDCl_3$): signals at 6.35 (ABq, 2H, $C_2$—$H_2$), 4.78 (2d, 2H, $C_6$—H and $C_7$—H), 3.05 (s, 1H, ester CH) and 2.65 (s, 10H, aromatic H).

EXAMPLE 31

Following the 7-acyl side chain cleavage reaction conditions described in Example 30 p-nitrobenzyl 7-amino-3-fluoro-3-cephem-4-carboxylate was prepared with the intermediate of Example 27, p-nitrobenzyl 7-[2-(2-thienyl)acetamido-3-fluoro-3-cephem-4-carboxylate.

EXAMPLE 32

Following the 7-acyl side chain cleavage reaction procedure described by Example 30 diphenylmethyl 7-amino-3-bromo-3-cephem-4-carboxylate is prepared with diphenylmethyl 7-phenoxyacetamido-3-bromo-3-cephem-4-carboxylate.

EXAMPLE 33

7-(D-Mandelamido)-3-chloro-3-cephem-4-carboxylic acid.

To a suspension of 812 mg. (2 mmole) of p-nitrobenzyl 7-amino-3-chloro-3-cephem-4-carboxylic acid hydrochloride in 40 ml. of ethyl acetate was added a solution of 520 mg. (5 mmole) of sodium bisulfite in 40 ml. of water. The mixture was vigorously stirred while 395 mg. (2.2 mmole) of D-mandelic acid O-carboxy anhydride were added. The mixture was stirred for 1.5 hours at room temperature and the aqueous layer was separated from the ethyl acetate layer and washed with ethyl acetate. The ethyl acetate wash was combined with the ethyl acetate layer and the combined wash and ethyl acetate layer were washed several times with water and then dried and evaporated to yield the reaction product as a dry residue. The residue was triturated with ether to yield 685 mg. of p-nitrobenzyl 7-(D-mandelamido)-3-chloro-3-cephem-4-carboxylate melting at about 158°–164°C. with decomposition.

Elemental analysis for $C_{22}H_{18}N_3O_7SCl$: Theory: C, 52.44; H, 3.60; N, 8.34; Cl, 7.04%. Found: C, 52.25; H, 3.45; N, 8.58; Cl, 6.82%.

NMR ($CDCl_3$): signals at 6.24 (ABq, 2H, $C_2$—$H_2$), 5.0–4.7 (m, 2H, $C_6$—H and $\alpha$—H), 4.57 (s, 2H, ester $CH_2$), 6.23 (q, 1H, $C_7$—H), and 2.8–1.2 —NH) (m, 10H, aromatic H and $C_7$-NH) tau.

UV (acetonitrile): $\lambda$ max 265 m$\mu$—NH) ($\epsilon$ = 18,600).

The reaction product, 200 mg., was reacted with hydrogen in the presence of 5% palladium on carbon to effect removal of the p-nitrobenzyl ester group and provide 75 mg. of 7-(D-mandelamido)-3-chloro-3-cephem-4-carboxylic acid.

NMR (D$_2$O-sodium bicarbonate): signals at 6.42 (ABq, 2H, C$_2$—H$_2$), 4.90 (d, 1H, C$_6$—H), 4.68 (s, 1H, α-CH, 4.37 (d, 1H, C$_7$—H) and 2.49 (s, 5H, aromatic H) tau.

EXAMPLE 34

7-[O-(Formyl)-D-mandelamido]-3-chloro-3-cephem-4-carboxylic acid.

p-Nitrobenzyl 7-amino-3-chloro-3-cephem-4-carboxylate, 2.2 g. (5.9 mmole) was acylated with 1.08 mg. (6mmole) of O-formyl mandelic acid in dry tetrahydrofuran in the presence of 1.5 g. (6mmole) of the condensing agent E.E.D.Q. to provide 2 g. (65 percent yield) of the product p-nitrobenzyl 7-[O-(formyl)D-mandelamido]-3-chloro-3-cephem-4-carboxylate. The product was obtained crystalline from ethyl acetate.

Elemental analysis calculated for C$_{33}$H$_{18}$ClN$_3$O$_8$S: Theory: C, 51.93; H, 3.41; N, 7.90; Cl, 6.67 percent. Found: C, 52.13; H, 3.27; N, 7.88; Cl, 6.88 percent.

Nuclear magnetic resonance spectrum (CDCl$_3$) showed signals at 6.40 (ABq, 2H, C$_2$—H$_2$), 4.97 (d, 1H, C$_6$—H), 4.62 (s, 2H, ester—CH$_2$), 4.20 (q, 1H, C$_7$—H), 3.75 (s, 1H, α—CH), and 2.75–1.72 (m, 1OH, aromatic H and 0—CHO) tau.

The above acylated ester product was de-esterified by hydrogenolysis of the p-nitrobenzyl ester group over prereduced 5 percent palladium-on-carbon catalyst by following the procedures described in the preceding Examples. From 2.0 g. (3.76 mmole) of the ester 1.2 g. of the product 7-[O-(formyl)-D-mandelamido]-3-chloro-3-cephem-4-carboxylic acid, were obtained.

Electrometric titration (66 percent aqueous DMF). showed a titratable group having a pKa of 4.5. The apparent molecular weight was 405. The calculated molecular weight is 397. U.S. (acetonitrile); λ max 265 mμ (ϵ=7800).

The nuclear magnetic resonance spectrum of the product run in deuterated dimethyl sulfoxide (DMSO d$_6$) was consistent with the structure of the product:

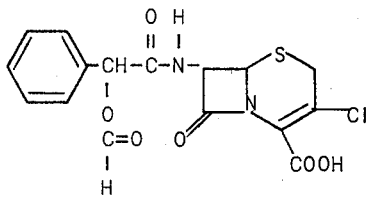

EXAMPLE 35

This example demonstrates the preparation of a 3-halo-3-cephem compound with a 3-exomethylenecepham compound without the isolation and purification of the 3-hydroxy-3-cephem intermediate.

A solution of 1 g. (2 mmole) of p-nitrobenzyl 7-phenoxyacetamido-3-exomethylenecepham-4-carboxylate in methylene chloride was cooled to −78°C. and was ozonized. The ozonide was decomposed with sulfur dioxide and the solvent evaporated under reduced pressure. The crude residue was comprised of about 85 percent of the 3-hydroxy-3-cephem ester as estimated from the nmr spectrum of the residue run in deuterated dimethylsulfoxide.

The crude 3-hydroxy-3-cephem ester was reacted in dimethylformamide with phosphorus pentachloride to provide 1.4 g. of p-nitrobenzyl 7-phenoxyacetamido-3-chloro-3-cephem-4-carboxylate. The nmr spectrum of the product run in DMSO d$_6$ compared with that of the previously prepared compound. The overall yield of the product as calculated from the 3-exomethylenecepham ester was 46 percent.

I claim:

1. A compound of the formula

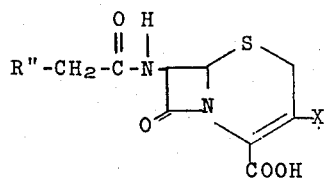

wherein R″ is 2-thienyl, 3-thienyl, 2-furyl, 2-oxazolyl, 2-thiazolyl, or 1-tetrazolyl;

X is chloro or bromo;

or the non-toxic pharmaceutically acceptable salts thereof.

2. The compound of claim 1 wherein R″ is 2-thienyl, 3-thienyl, 2-furyl or 1-tetrazolyl and X is chloro.

3. The compound of claim 2 said compound being 7-[2-(2-thienyl) acetamido]-3-chloro-3-cephem-4-carboxylic acid.

4. The compound of claim 1 wherein [R″ is 2-thienyl and] X is bromo.

5. The compound of claim 4 said compound being 7-[2-(2-thienyl)acetamido]-3-bromo-3-cephem-4-carboxylic acid.

* * * * *